（12） United States Patent
Gies

(10) Patent No.: US 9,030,195 B2
(45) Date of Patent: May 12, 2015

(54) LINEAR STRUCTURE INSPECTION APPARATUS AND METHOD

(75) Inventor: Paul D. Gies, Redwood Meadows (CA)

(73) Assignee: Athena Industrial Technologies, Inc. (CA)

( * ) Notice: Subject to any disclaimer, the term of this patent is extended or adjusted under 35 U.S.C. 154(b) by 1719 days.

(21) Appl. No.: 12/520,643

(22) PCT Filed: Dec. 20, 2007

(86) PCT No.: PCT/CA2007/002359
§ 371 (c)(1),
(2), (4) Date: Oct. 28, 2010

(87) PCT Pub. No.: WO2008/074161
PCT Pub. Date: Jun. 26, 2008

(65) Prior Publication Data
US 2012/0038354 A1    Feb. 16, 2012

Related U.S. Application Data

(60) Provisional application No. 60/871,320, filed on Dec. 21, 2006.

(51) Int. Cl.
G01N 27/82       (2006.01)
G01N 27/90       (2006.01)
F16L 101/30      (2006.01)

(52) U.S. Cl.
CPC ............. *G01N 27/902* (2013.01); *G01N 27/82* (2013.01); *F16L 2101/30* (2013.01)

(58) Field of Classification Search
CPC ........... F16L 55/46; F16L 55/48; F16L 55/28; F16L 55/26; F16L 55/1283; F16L 2101/30; B08B 9/0557; B08B 9/0553; B08B 9/0554; B08B 9/0555; B08B 9/0552; G01M 3/005; G01M 3/2823; G01M 3/246; G01N 2291/2636; G01N 2291/106; G01N 29/265; G01N 27/902; E21B 37/00; B05B 12/1481; G01P 3/60

USPC .......................................... 324/220, 221, 240
See application file for complete search history.

(56) References Cited

U.S. PATENT DOCUMENTS

| 3,755,908 | A | * | 9/1973 | VerNooy ....................... 33/544.3 |
| 4,009,614 | A | * | 3/1977 | Sheppard et al. ................ 73/195 |
| 4,350,955 | A | * | 9/1982 | Jackson et al. ................. 324/303 |
| 4,717,875 | A | * | 1/1988 | Lara ............................... 324/220 |
| 4,769,598 | A | * | 9/1988 | Krieg et al. .................... 324/219 |
| 4,789,827 | A | * | 12/1988 | Bergander ..................... 324/220 |
| 5,293,117 | A | * | 3/1994 | Hwang .......................... 324/220 |
| 5,454,276 | A | * | 10/1995 | Wernicke ..................... 73/865.8 |
| 5,471,140 | A | * | 11/1995 | Hanley .......................... 324/303 |
| 5,532,587 | A | * | 7/1996 | Downs et al. ................. 324/220 |
| 5,565,633 | A | * | 10/1996 | Wernicke ..................... 73/865.8 |
| 5,779,948 | A | * | 7/1998 | Perkins et al. .................. 264/35 |
| 5,864,232 | A | * | 1/1999 | Laursen ......................... 324/220 |
| 6,067,846 | A | * | 5/2000 | Hill et al. .......................... 73/82 |
| 6,087,830 | A | * | 7/2000 | Brandly et al. ................ 324/220 |
| 6,100,684 | A | * | 8/2000 | Ramaut .......................... 324/220 |
| 6,538,431 | B2 | * | 3/2003 | Couchman et al. ............ 324/220 |
| 6,847,207 | B1 | * | 1/2005 | Veach et al. ................... 324/220 |
| 6,995,515 | B2 | * | 2/2006 | Rostoker et al. ........ 315/111.21 |
| 7,256,576 | B2 | * | 8/2007 | Mandziuk et al. ............ 324/220 |
| 7,475,591 | B2 | * | 1/2009 | Buckley et al. ................ 73/49.5 |
| 8,291,780 | B2 | * | 10/2012 | Smith et al. ................... 73/865.8 |
| 2003/0052670 | A1 | * | 3/2003 | Miszewski .................... 324/228 |
| 2007/0022830 | A1 | * | 2/2007 | Mandziuk et al. ........... 73/865.8 |
| 2007/0113622 | A1 | * | 5/2007 | Buckley et al. ..................... 73/49 |

FOREIGN PATENT DOCUMENTS

| CA | 2235063 | 10/1998 |
| CA | 2 245 419 | 3/1999 |
| CA | 2245419 A1 | 3/1999 |
| CA | 2 596 148 | 8/2006 |
| CA | 2596148 A1 | 8/2006 |
| DE | 10 2004 054423 B3 | 5/2006 |
| WO | WO 99/00621 | 1/1999 |
| WO | WO 99/00621 A1 | 1/1999 |
| WO | WO 2004/035368 | 4/2004 |
| WO | WO 2004/035368 A1 | 4/2004 |

OTHER PUBLICATIONS

Canadian Office Action dated Aug. 17, 2011 issued in Canadian Application No. 2,571,893.
Canadian Office Action dated Dec. 19, 2011 issued in Canadian Application No. 2,571,893.
Canadian Office Action dated May 11, 2012 issued in Canadian Application No. 2,571,893.
Canadian Office Action dated Nov. 13, 2012 issued in Canadian Application No. 2,571,893.
Canadian Office Action dated Apr. 4, 2013 issued in Canadian Application No. 2,571,893.
Canadian Office Action dated Jan. 12, 2012 issued in Canadian Application No. 2,757,488.
Canadian Office Action dated May 22, 2012 issued in Canadian Application No. 2,757,488.
International Search Report dated Apr. 7, 2008 issued in PCT International Application No. PCT/CA2007/002359.
International Search Report dated Apr. 7, 2008, issued in corresponding international application No. PCT/CA2007/002359.
Supplementary European Search Report dated Apr. 28, 2014 issued in European Application No. 07855639.6.

* cited by examiner

* cited by examinerCanadian Office Action dated Nov. 19, 2010 issued in Canadian Application No. 2,571,893.

(Continued)

*Primary Examiner* — Jay Patidar
*Assistant Examiner* — Sean Curtis
(74) *Attorney, Agent, or Firm* — Ostrolenk Faber LLP

(57) ABSTRACT

An apparatus is provided for sensing anomalies in a long electrically conductive object to be inspected. The object may be a pipeline, or other hollow tube. The apparatus may have a magnetic field generator, and an array of sensors spaced about the field generator. As relative motion in the longitudinal direction occurs between the apparatus and the object to be inspected, the moving magnetic field, or flux, passed from the field generator into the object to be inspected may tend to cause eddy currents to flow in the object. The sensors may be spaced both axially and circumferentially to permit variation in magnetic flux, or eddy current divergence, to be sensed as a function of either or both of axial position relative to the wave front of the magnetic field (or, effectively equivalently any other known datum such as the radial plane of the midpoint of the field generator), and circumferential position about the periphery of the apparatus as measured from an angular datum. Post processing calculation may then tend to permit inferences to be drawn about the location, size, size, shape, and perhaps nature, of anomalies in the object. The sensors, and possibly the entire field generator, may be maintained at a standoff distance from the object to be inspected, as by a sealed housing such as may protect the sensors and reduce the need for and cost of maintenance. The field generator may include two primary poles of like nature held in a non-touching back to back orientation, and may include secondary magnetic circuits placed to bias the flux of the primary magnetic circuit into a more focussed shape with respect to the object to be inspected.

25 Claims, 11 Drawing Sheets

LINEAR STRUCTURE INSPECTION APPARATUS AND METHOD

CROSS REFERENCE TO RELATED APPLICATIONS

The present application is a 35 U.S.C. §371 National Phase conversion of PCT/CA2007/002359, filed Dec. 20, 2007, which claims benefit of U.S. Provisional Application No. 60/871,320, filed Dec. 21, 2006, the disclosure of which is incorporated herein by reference. The PCT International Application was published in the English language.

FIELD OF THE INVENTION

This invention relates to the field of non-destructive defect detection apparatus.

BACKGROUND OF THE INVENTION

Defect or anomaly detection in structures is often important in determining maintenance intervals, or for determining whether structures require repair or replacement. Non-destructive detection of structural anomalies may be desired, and the ability to perform timely and effective examination of objects may not necessarily be made easier when the objects are large, may be remotely located relative to large population centers, and may be subject to harsh geographic or climatic conditions.

By way of example, the inspection of pipelines is a task of some interest and economic importance, in particular as it pertains to pipelines for carrying hydrocarbon gases and oils, although pipelines for transporting other fluids and slurries are also known. A typical pipeline for carrying gas, oil or water may run for many miles between pumping stations. The pipeline may be exposed to the weather. That weather may include a corrosive atmosphere, be it a salt spray environment or some other. The pipeline may run through regions of greater or lesser humidity. There may be extremes of heat and cold. In some places the pipeline may be carried above ground on spaced supports. In others it may be buried, or partially buried. In locations in which the pipeline is buried, the surrounding stratum may have a high or low moisture content, and may be alkaline or acidic. The fluid, or slurry to be carried in the pipeline may itself not be benign, but may be of an aggressive nature, and may be abrasive or corrosive, or both. The material flowing in the pipeline may be under significant pressure, perhaps in the thousands of psi., and may be at an elevated temperature, possibly in the range of 80-100 C. This environment may effect not only the life of the pipeline and the nature of the defects that may be expected to be found in a section of pipe over time, but also the tools used for monitoring and maintaining the pipeline. Stress cracking and stress corrosion may occur or be hastened by movement related to temperature change, earthquakes or tremors, ground settling, vibration from fluid movement, and pressure changes in the medium during operation.

Pipelines are subject to many different kinds of defects. There may be internal or external corrosion. There may be fatigue cracks, most typically externally initiating. There may be cracks or inclusions in the welded joints near flange connections. There may be dents or cracks caused by external factors. There my be an out of round, or ovality, condition. It may be that a defect in the pipewall of a pipeline may be relatively benign, and may not be life limiting. It may be of a size that may permit scheduled removal at the next convenient maintenance interval, rather than immediate removal on a more urgent, and costly, basis. Inasmuch as the removal and replacement of, for example, buried pipe in a remote location may not be overly convenient, knowledge of whether a pipe is at or near a certain defect size limit may be quite helpful.

It is known to monitor the condition of pipelines by passing monitoring tools down the pipe. Such tools tend generically to be known as pipeline "pigs". A "pig" is somewhat of a plug, or slug, that fits within the pipe and has a generally squat shape—namely a relatively low length to diameter ratio—that may permit the pig to get around bends in the pipe. A pig may be a "dumb pig" or an "intelligent pig". An intelligent pig usually has sensing and recording equipment. The general manner of operation is that the pig is inserted into the flow path, and then the flow of fluid carries the pig along the pipe. Usually the pig has a body, and the body has one or more seal rings or skirts (usually one upstream and one downstream) such as may tend to wipe along the pipewall, and for which the conventional terminology is a "cup". The cups tend to be consumable polyurethane skirts that are replaced after each run through a pipeline section. It may be that more than one pig may be sent down the pipeline at the same time, with the pigs being hooked together in a train like manner at articulations. These articulations permit the train of pigs to pass through corners in the pipeline. One reason why more than one pig may be employed is that a second pig may carry the electrical power source (e.g., batteries) for the electrical equipment carried by the "intelligent" pig. When the pig is inserted, a pressure build-up behind the upstream seal (and a reduction below the downstream seal, as may be), causes the pig to be carried along, such that the motive power for pig operation, and the speed at which the pig moves, are dictated by the pumping power of the fluid driving pump. Typical fluid speeds may vary greatly, from perhaps as low as 0.5 m/s to about 10 m/s for a liquid, and perhaps 5 m/s to 50 m/s for a gas.

The measurement of defects in pipelines poses a number of challenges. First, it may be helpful to be able to differentiate between, for example, a build up of corrosion, and a fatigue crack, or between either of them and a dent. Second, an intelligent pig may have a large power requirement, it has to travel with a big power supply or it can only go a relatively short distance in the pipe before it must be removed, and the power supply replaced or recharged. Alternatively, the amount of data to be recorded my be too great, and periodic removal and downloading may be required. Further, where portions of the pig, such as brushes (e.g., electromagnetic brushes of feeler gauges), contact the pipewall during motion, or where sensors are carried in a relatively exposed manner, the maintenance required to overhaul the pig in preparation for its next run through the pipe may in itself be an expensive, laborious and time consuming task. The post-run signal processing may itself be quite an undertaking, and may not yield results for several days. An improvement in any one of these things would be welcome—be it a reduction in power consumption, real time signal processing that reduces the amount of data to be stored, a reduction in maintenance requirements, an improvement in the resolution of the size of defect that can be detected, or an improvement in the ability to discriminate between types of defects.

SUMMARY OF THE INVENTION

In an aspect of the invention there is an intelligent pig for insertion in a pipeline. The intelligent pig has a body and sensors mounted within the body. The sensors are operable from within the body to monitor properties of the pipeline while the intelligent pig is within the pipeline and the sensors are enclosed within the body.

In another feature of that aspect of the invention, the body has a closure member by which the sensors may be sealed within the body. In another feature the sensors are at least one of (a) electrical sensors; (b) magnetic sensors; and the body includes a shell that is substantially electro-magnetically transparent. In still another feature, the pig has at least one of (a) ends that are narrowed relative to the body more generally; and (b) ends having resilient pipe wall following cups mounted adjacent thereto. In another feature, there is a combination of the intelligent pig and a trailing pig connected thereto. In a further feature, the trailing pig houses at least one of (a) a power supply; (b) batteries; (c) data recording equipment; (d) data transmission equipment; and (e) location logging equipment.

In yet another feature of that aspect of the invention, the pig includes a magnetic field emitting circuit. Alternatively expressed, the pig includes a magnetic field generator. In another feature, the magnetic field generator includes first and second poles of the same magnetic polarity forced into non-touching proximity with each other. In still another feature, the pig includes at least one primary magnetic circuit and at least one secondary magnetic circuit path. In yet another feature, the pig includes magnetic flux sensing equipment. In a further feature the pig includes eddy current divergence sensors. In still another feature the magnetic field flux sensing equipment is mounted peripherally about the magnetic field generator, and is operable to sense sectoral magnetic flux variation. In one variation, the pig has a conduit running lengthwise therethrough to permit the passage of production fluid carried in the pipeline.

In yet another feature, the body comprises a closure member by which the sensors may be sealed within the body. The sensors include at least one of (a) electrical sensors; (b) magnetic sensors. The body includes a shell that is substantially electro-magnetically transparent. The pig has at least one of (a) ends that are narrowed relative to the body more generally; and (b) ends that have resilient pipe wall following cups mounted adjacent thereto. The pig includes a magnetic field generator for passing magnetic flux into the pipeline. The magnetic field generator includes at least one primary magnetic circuit and at least one secondary magnetic circuit. The pig includes magnetic flux sensing equipment. The magnetic flux sensing equipment includes eddy current divergence sensors. The magnetic field flux sensing equipment is mounted peripherally about the magnetic field generator, and is operable to sense sectoral magnetic flux variation.

In another aspect of the invention, there is a pipeline pig for operation within a pipeline, the pipeline having a pipe wall. The pig has a magnetic field generator mounted to pass a magnetic flux field into the pipe wall when the pig is within the pipeline, magnetic flux field sensing equipment mounted adjacent to the flux generator, and a standoff mounted to prevent the sensors from touching the pipe wall.

In a feature of that aspect of the invention, the pig has a body, the body includes a shell, the sensing equipment is mounted within the shell, and the standoff includes at least a portion of the shell. In another feature the shell encloses the sensing equipment. In yet another feature the magnetic field flux sensing equipment is mounted peripherally about the magnetic field generator, and is operable to sense sectoral magnetic flux variation.

In a further aspect of the invention there is an apparatus for detecting anomalies in an electrically conductive structure that has a ratio of length to girth in excess of 20:1, the apparatus being movable in the lengthwise direction relative to the structure. The apparatus has a magnetic field generator. The magnetic field generator includes a primary magnetic circuit oriented to pass a magnetic flux into the structure along a wave front that extends predominantly cross-wise to the longitudinal direction when the apparatus is moved in the longitudinal direction. The apparatus includes a magnetic flux sensing array. The magnetic flux sensing array includes flux sensors spaced sectorally adjacent to the magnetic field generator. The array extends in a direction predominantly aligned with the wavefront or fieldfront.

In another feature the structure has a peripheral profile cross-wise to the longitudinal direction, and the magnetic field generator includes a pole piece having a mating profile corresponding to the profile of the structure. In yet another feature the structure is a rail road rail, the rail has a profile, and the magnetic field generator has at least one pole piece having a profile corresponding to at least a portion of the profile of the rail. In a further feature the apparatus meets one of the following conditions: (a) the apparatus has a closed form, inwardly facing pole piece profile having a passage formed therethrough to permit axial motion of the structure; and (b) the structure is hollow and has a closed form periphery, and the apparatus has an outwardly facing peripheral pole piece profile to permit passage of the apparatus within the hollow structure. In another feature the magnetic field generator includes first and second primary magnetic circuits, the first and second magnetic circuits are mutually segregated from each other; the first and second circuits each have a first pole, the respective first poles being mutually repulsive, and the first poles are being positioned closely adjacent to each other.

In another feature the magnetic field generator includes at least one primary magnetic circuit, and a least one secondary magnetic circuit, the secondary magnetic circuit being positioned to bias magnetic flux from the first magnetic circuit to pass into the structure. In a further feature the magnetic field generator includes at least a first primary magnetic circuit. The primary magnetic circuit has a first pole. The magnetic field generator includes two secondary magnetic circuits. The secondary magnetic circuits each have a first pole. The first poles of the primary magnetic circuit and the first poles of the respective secondary magnetic circuits all being mutually repulsive. The first pole of the primary magnetic circuit being sandwiched between the respective first poles of the secondary magnetic circuits. In another feature, the magnetic field generator includes a second primary magnetic circuit, the second primary magnetic circuit has a first pole, and the first poles of the first and second primary magnetic circuits are mutually repulsive. The first poles of the first and second primary magnetic circuits are closely spaced apart, and the first poles of the primary magnetic circuits are bracketed by the first poles of the secondary magnetic circuits. In another feature the apparatus includes a standoff mounted to prevent the flux sensors from contacting the electrically conductive structure. In another feature the apparatus being enclosed within a shell. In another feature the apparatus being a pipeline pig.

In a further aspect of the invention, there is a pipeline pig for insertion in a pipeline that has an electrically conductive wall. The pig includes a magnetic field generator for passing magnetic flux into the pipeline wall. The magnetic flux generator includes a first magnetic circuit and a second magnetic circuit. The first and second magnetic circuits are segregated from each other. Each of the first and second magnetic circuits has a respective first pole, the first poles of the first and second magnetic circuits being placed next adjacent to each other. The first poles of the first and second magnetic circuits are mutually repulsive.

In a feature of that aspect of the invention, the first and second magnetic circuits are primary magnetic circuits, and the pig includes first and second secondary magnetic circuits. Each of the secondary magnetic circuits has a respective first pole. The first poles of the first and second primary circuits and the first poles of the secondary magnetic circuits are all mutually repulsive. The first poles of the first and second primary circuits being bracketed by the first poles of the first and second secondary circuits. In another feature, there is an array of magnetic flux sensors mounted about the magnetic field generator. The flux sensors are operable to permit independent monitoring of magnetic flux at a plurality of sectors about the magnetic field generator. In another feature the flux sensors are operable to sense magnetic flux as a function of circumferential position. In still another feature, the pig has a longitudinal axis defining an axial direction, and a periphery radially distant from the axis. The sensors are mounted circumferentially about the periphery; and the sensors are operable to sense axial variation in magnetic flux relative to the first poles of the first and second magnetic circuits. In still another feature, the pig has a longitudinal axis defining an axial direction, and a periphery radially distant from the axis. The sensors are mounted circumferentially about the periphery. The sensors are operable to sense axial variation in magnetic flux relative to the first poles of the first and second magnetic circuits. The flux sensors are operable to sense magnetic flux as a function of circumferential position.

In yet another feature, the sensors include at least a first set of sensors and a second set of sensors, the first set of sensors being mounted about the magnetic field generator in a first orientation relative to the magnetic field generator, and the second set of sensors being mounted about the magnetic field generator in a second orientation. Combined readings of sensors in the first and second sets of sensors permit radial and axial components of magnetic flux to be sensed in at least two of the plurality of sectors. In another feature, the first set of sensors includes sensors lying predominantly in a circumferential-axial orientation, and the second set of sensors including sensors lying in an orientation that being angularly skewed relative to the circumferential-axial orientation. In another feature the sensors of the second set of sensors are oriented substantially at right angles to the sensors of the first set of sensors.

In still another feature, the first poles of the first and second magnetic circuits lie to either side of a radially extending plane, and the sensors include a first set of sensors and a second set of sensors, the first set of sensors being oriented to lie predominantly in a radial plane, and the second set of sensors being oriented to lie predominantly in a circumferential-axial surface. In yet another further feature, the pig has a longitudinal centerline, the first poles of the first and second magnetic circuits lie to either side of a plane extending radially from the centerline, and the sensors include a first set of sensors and a second set of sensors, the first set of sensors being oriented to lie predominantly in a conical surface relative to the centerline, and the second set of sensors being oriented to lie in other than the conical surface. In still another feature, the conical surface is a first conical surface whose apex intersects the longitudinal centerline to one side of the radially extending plane, and the second set of sensors lies in a second conical surface whose apex lies to the other side of the radially extending plane. In another alternate feature, the array of flux sensors includes sensors differentially positioned in both axial and circumferential directions. In another feature the array includes sensors mounted to observe eddy field divergence in the pipeline wall. In another feature, the pig includes a standoff positioned to prevent the array of sensors from contacting the pipeline wall. In another feature the array of sensors is enclosed within a housing of the pig.

In still another aspect of the invention, there is a pipeline pig having a magnetic field generator. The magnetic field generator includes a primary magnetic circuit having a first pole and a pair of secondary magnetic circuits segregated from the primary magnetic circuit. The secondary magnetic circuits each have a respective first pole. The first poles of the secondary magnetic circuits and the first pole of the primary magnetic circuit are all mutually repulsive, and the first pole of the primary magnetic circuit being sandwiched between the first poles of the secondary magnetic circuits.

In a further feature, the pig has an array of magnetic flux sensors mounted about the field generator. The sensors are operable to monitor sectoral flux variation about the field generator. In still another feature the sensors are operable to monitor both axial and circumferential flux variation. In yet another feature the pig has a housing and the housing encloses the sensors.

In still yet another aspect of the invention there is a pipeline pig for insertion within a pipeline, the pipeline having an electrically conductive circumferential wall. The pipeline pig has a magnetic field generator operable to induce eddy currents in the wall of the pipeline as the pig passes thereby. The pig has an array of sensors mounted thereabout, the array of sensors being operable to monitor magnetic flux about the flux generator as a function of axial and circumferential position.

BRIEF DESCRIPTION OF THE ILLUSTRATIONS

The invention may be explained with the aid of the accompanying illustrations, in which:

FIG. 2b shows an alternate embodiment of pipeline pig on a longitudinal section analogous to that of FIG. 2a;

FIG. 2c shows another alternate embodiment of pipeline pig on a longitudinal section analogous to that of FIG. 2a;

FIG. 2d shows a general view of a pig train, such as might include the pig of FIG. 2a;

DETAILED DESCRIPTION

Figure 1A:
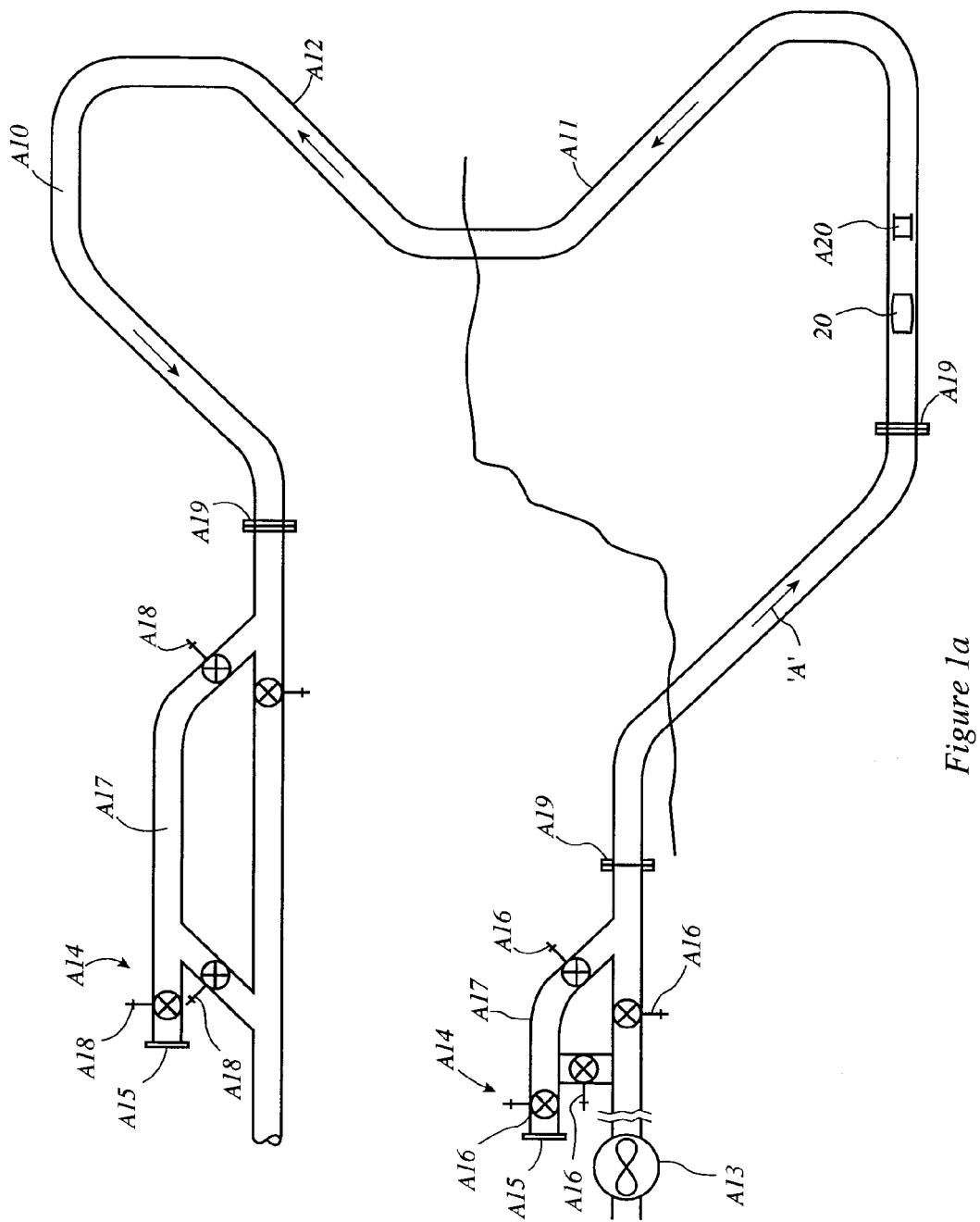
FIG. 1a is a general representation of a pipeline environment establishing an example of one context to which the description of the invention which follows may apply.

The description that follows, and the embodiments described therein, are provided by way of illustration of an example, or examples, of particular embodiments of the principles of the present invention. These examples are provided for the purposes of explanation, and not of limitation, of those principles and of the invention. In the description, like parts are marked throughout the specification and the drawings with the same respective reference numerals. The drawings are not necessarily to scale and in some instances proportions may have been exaggerated, the more clearly to depict certain features of the invention.

The terminology used in this specification is thought to be consistent with the customary and ordinary meanings of those terms as they would be understood by a person of ordinary skill in the art in North America. Following from the decision of the Court of Appeal for the Federal Circuit in Phillips v. AWH Corp., the Applicant expressly excludes all interpretations that are inconsistent with this specification, and, in particular, expressly excludes any interpretation of the claims or the language used in this specification such as may be made in the USPTO, or in any other Patent Office, other than those interpretations for which express support can be demonstrated in this specification or in objective evidence of record in accordance with In re Lee, (for example, earlier publications by persons not employed by the USPTO or any other Patent Office), demonstrating how the terms are used and understood by persons of ordinary skill in the art, or by way of expert evidence of a person or persons of experience in the art.

This description discusses various embodiments of a pipeline pig 20. By way of general overview, the apparatus described herein includes a sensing assembly for detecting anomalies in an electrically conductive material. The inspection unit may also include a data processing capability to permit eddy field anomaly data taken at several locations to be correlated in a manner tending to permit estimation of the location, size, shape, and nature of anomalies detected in the substrate.

In terms of general orientation, it may be helpful to consider a polar cylindrical co-ordinate system. The axial or longitudinal direction, or x-axis, may be taken as the longitudinal centerline of pig 20, or, roughly equivalently, of the pipeline, which, even if not co-linear, may be thought of as being generally parallel. To the extent that it may be pertinent, the positive x direction is in the direction of forward travel (i.e., positive axial or longitudinal travel) of pig 20 along the pipe, from an upstream starting point to a downstream finishing point. In the general conceptual sense, pig 20 may be thought of as being concentric with the pipeline, although this need not necessarily be precisely true. There is discussion of eccentricity of the pig relative to the pipeline, and also discussion of irregularities in the geometry of the pipewall, be it in terms of degree of ovality, dents or bulges. The radial direction, or r-axis, is measured perpendicular to, and away from, the longitudinal axis. The circumferential direction is the angular direction mutually perpendicular to both the longitudinal and radial directions, and may be measured from an arbitrary datum angle.

As a starting point, consider a length of pipeline, A10. Pipeline A10 may typically be made of a ferro-magnetic material, such as steel, and may be considered an object with a high aspect ratio of length to diameter. For the purposes of this description, the length:diameter ratio is greater than 20:1, probably greater than 100:1, and in many cases orders of magnitude larger. Parts of the pipeline may lie underground, as at A11, and parts may be carried above ground, as at A12. The fluid carried by the pipeline (which may include slurries, slug flows, two phase flows, long chain "flowing" polymer feed stocks, and any other flowable material) is urged in the direction of arrow 'A' by the pumping equipment of a pumping station, indicated generically as A13. In various locations, pipeline A10 may include access fittings, such as indicated generally at A14. A plate A15 may be opened to permit introduction of a pig into a secondary passageway. Manipulation of valves A16 may permit fluid to flow through the secondary passageway A17, and thus to carry the pig 20, into the main portion of the pipeline. Some distance downstream there may be another secondary passageway A17, and valves A18, permitting the pig to be removed. Along the way, pipeline A10 may have flanged couplings A19. The location of the flanged couplings is clearly both fixed and precisely known.

To begin generically, pipeline A10 may include a zone or region that includes a structural element A20. Element A20 may typically be considered to be a portion of a plate or a shell. Alternatively, it may be a portion of a railroad track, or a portion of a drill string. In some embodiments element A20 may tend, conceptually, to be a web or membrane that has relatively great extent in two directions (x and y in a Cartesian co-ordinate context), or longitudinal and circumferential, as might apply to a pipeline or pressure vessel, and of lesser extent in the third direction, namely that of plate thickness (the z direction in a Cartesian context, radial in a Cylindrical Polar co-ordinate context). Although structural element A20 may have the properties of a web or membrane for some purposes of structural analysis, (e.g., the wall of a pipeline) it will be assumed to have a finite, non-trivial thickness at the level of defect or anomaly detection that is of interest. It may be that examination is intended to reveal defects before a critical flaw size is reached.

Structural element A20 is electrically conductive, although it need not necessarily be ferro-magnetic, e.g., it may be made of a non-magnetic metal such as aluminum, or some other partially or modestly conductive material. Element A20 may have a protective coating A22. Protective coatings, such as coating A22, may be found on either the outside or the inside of the pipe, or both. Protective coating A22 is assumed for the purposes of this description to be electromagnetically inactive: it is neither ferro-magnetic, nor a conductor of electricity. Protective coating A22 is also assumed to be of a substantially uniform thickness, $t_{22}$, and it is assumed that $t_{22}$ is small, if not very small, as compared to the wall thickness of the plate to be measured, $t_{20}$. For whatever reason, it may not be desirable to remove coating A22. However, somewhere in element A20 there may be an anomaly A25 such as a flaw or defect that may, potentially, hold the seeds of catastrophic failure. It would, therefore, be desirable to find such a flaw or defect. For example, suppose that element A20 has an anomaly in the nature of a crack A24 that initiated at a crack initiation site on the outside or external surface A23 of element A20, and that has now grown to a certain size signified by length, $L_{24}$, and depth, $D_{24}$. Suppose also that element A20 has another anomaly in the nature of a void or an inclusion A26 that, again, may be located a certain depth from the surface and may have a certain width $W_{26}$, breadth $t_{26}$ and length, $L_{26}$. Further still, it may be that element A20 has an anomaly in the nature of a region of corrosion A28, in which a portion of the material adjacent to the inside A27 or outside A31 surface has been transformed to a non-conductive oxide, that region having an average depth, $D_{28}$, length, $L_{28}$, and width $W_{26}$. Region A28 may be on either the inside or the outside of the plate. Alternatively, the defect may be a zone of defects such as a colony of stress corrosion cracks, as at A29. Pipeline A10 may also have regions that include bulges or dents, as at A30, or non-oval portions, as at A32.

The body of pig 20 may tend to have a length that is greater than its diameter, perhaps in the range of 2½-4 times its diameter. Although pig 20 may pass through corners, or bends, most of the discussion will be made on the simplified basis of a body passing along an infinitely long, straight cylindrical (or substantially cylindrical) passageway, where the passageway has a wall that forms a continuous closed path about the pig in the circumferential direction, that path being both electrically and magnetically conductive.

The body may be a sealed shell 22, having forward and aft flexible skirts, or wipers, or cups, 24, 26 which may be made of a material such as polyurethane. As the pig travels along pipeline A10, cups 24 and 26 deflect rearwardly, their outer peripheral edges being elastically biased to ride against the inside of the pipe wall. Cups 24, 26 may be consumable wear items that are replaced when pig 20 is serviced. The drive cups are semi flexible plastic discs that are designed to seal against the pipe wall. This allows the pressure of the pipeline fluid or gas to drive the pig through the pipe. This movement in turn generates circumferential eddy currents as magnetic field generation devices pass by. In this manner the power of the pump station is used and not the tool batteries. As a result the tool batteries need only power the data recorder and sensor electronics. It should be noted that there are other options for generating eddy currents in pipe but the very high power requirement limits their usefulness in active pipeline inspection.

Pig 20 may include an end access plate 28, by which the innards of pig 20 may be installed or removed for maintenance, as may be required from time to time. Sealed shell 22 may be made of a non-ferro-magnetic material and non-electrically conductive material. That is, for the purposes of the discussion that follows, shell 22 is electro-magnetically transparent. Pig 20 is of such a length and shape, and maximum external diameter to permit it to pass along a pipe having bends in it. To that end, shell 22 may be wider at its waist as at 18, and narrower at its ends as at 19. The bends, typically, may tend not to have a smaller centerline bend radius than twice the diameter of the pipe. The overall diameter of pig 20 and cups 24, 26 may be such as to permit pig 20 to pass through large valves and flange couplings mounted along pipeline 20. In the illustration above the field generator has a dual taper. This allows the field generator to properly clear tight bends in the pipeline.

Figure 2A:
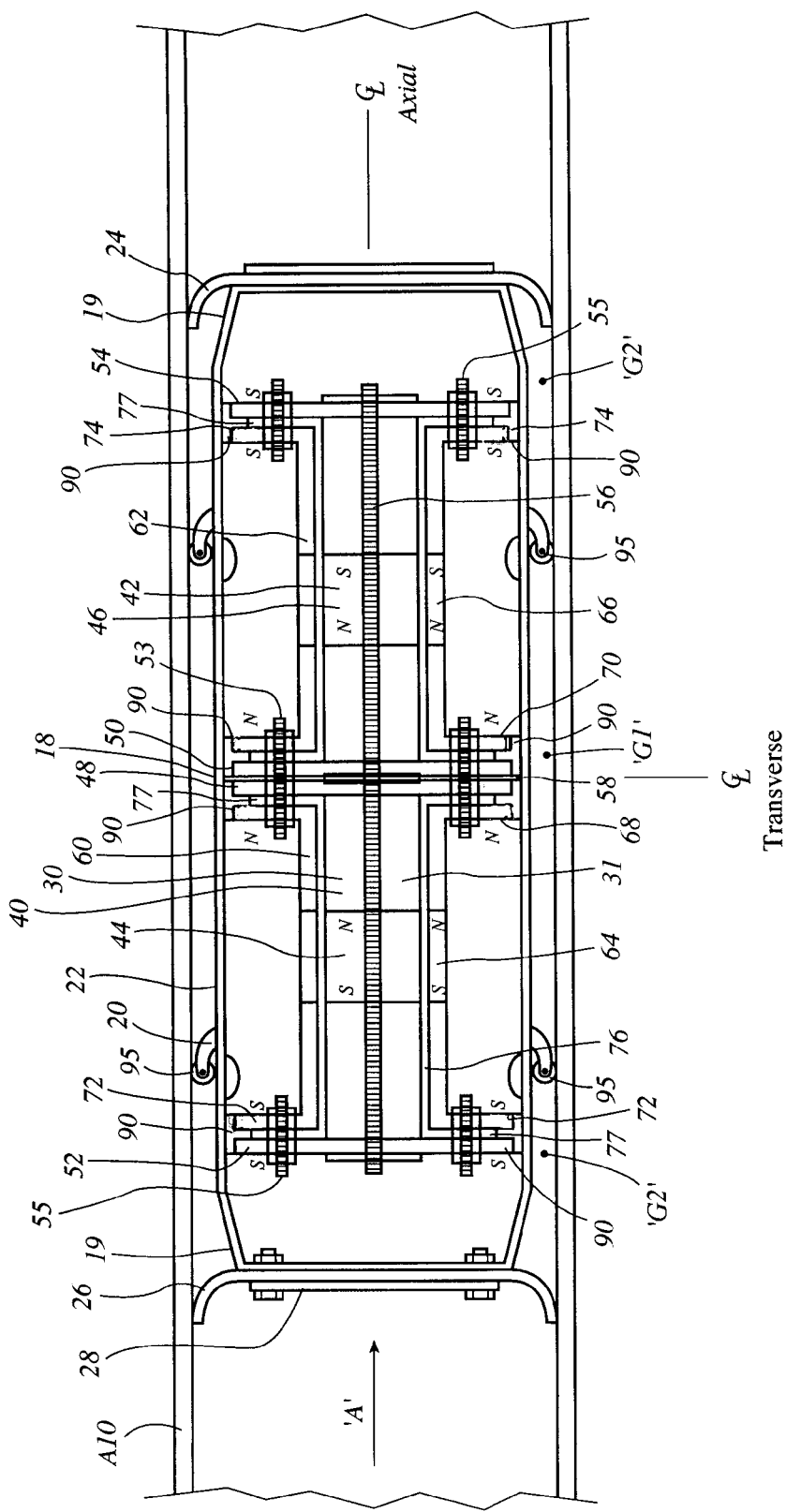
FIG. 2a shows a conceptual longitudinal cross-section of the pipeline pig of FIG. 1b taken on section '2a-2a'.
Figure 2B:
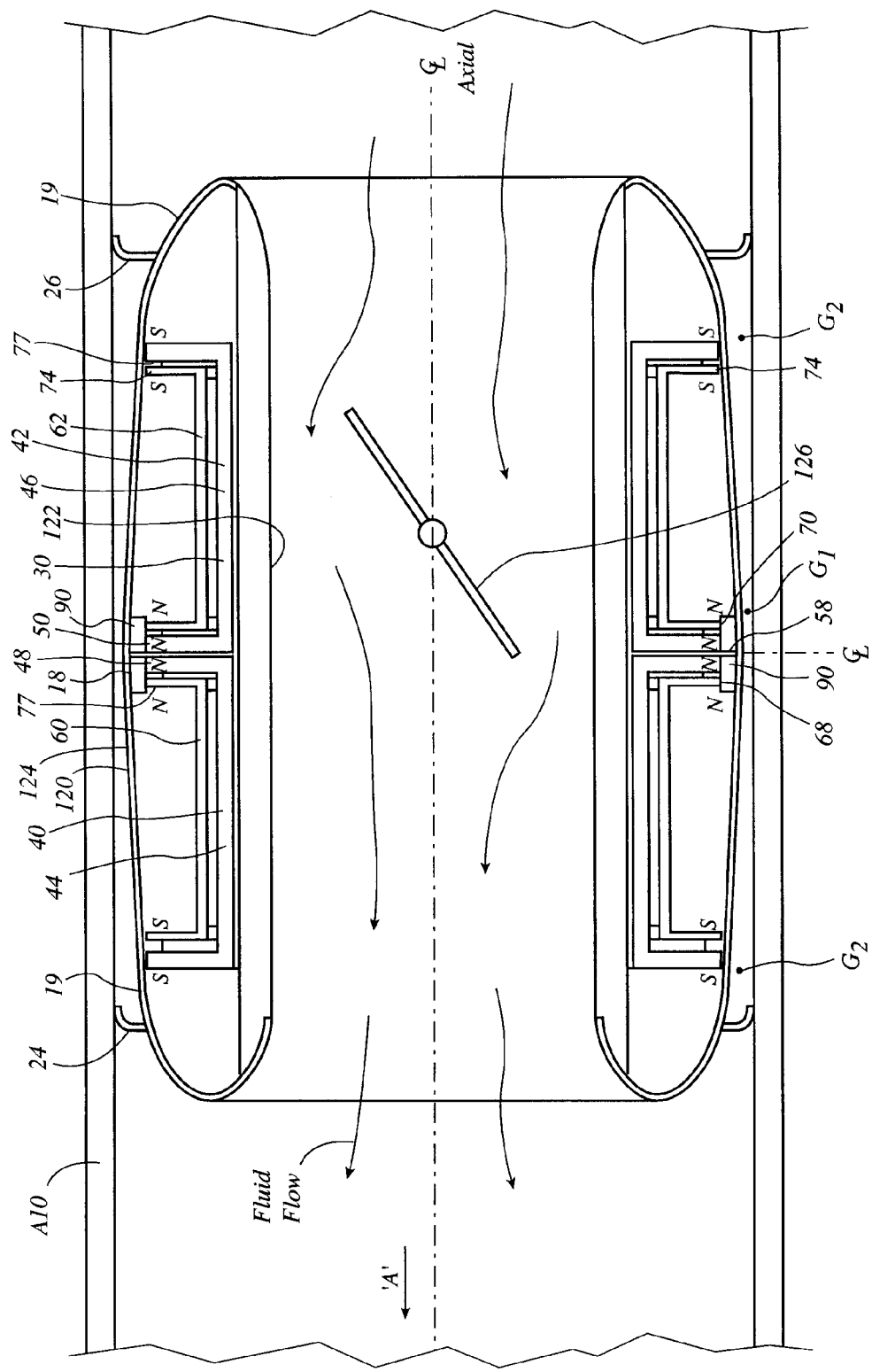
Figure 2C:
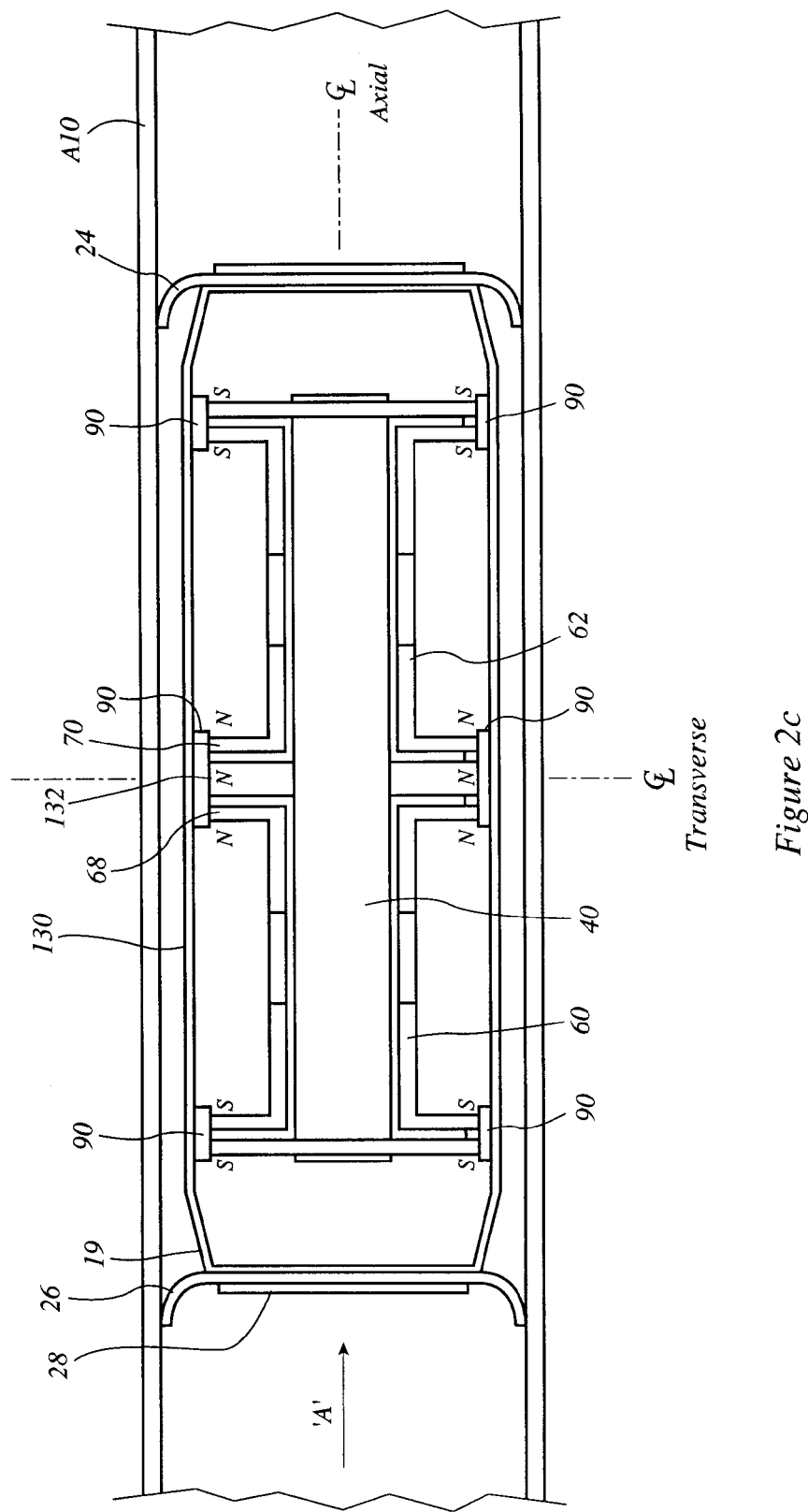
Figure 2D:
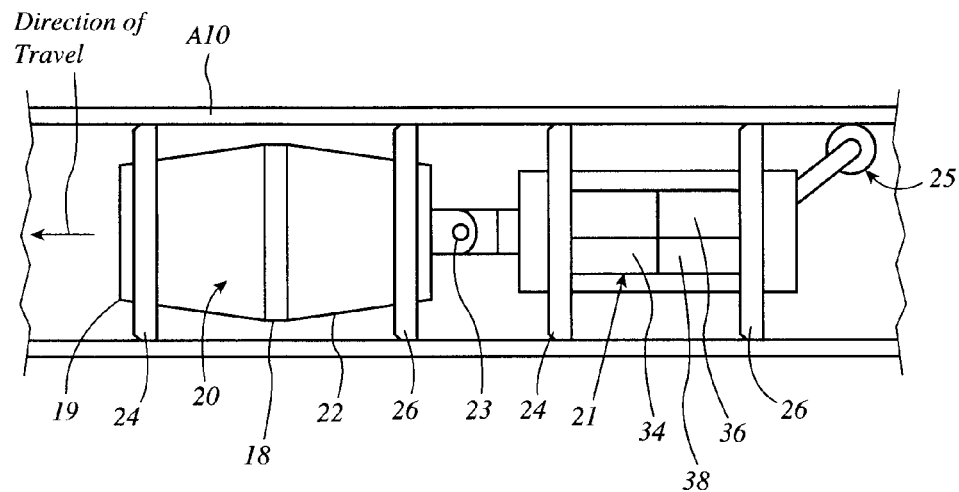

It may be that pig 20 is not a single unit, but rather includes a trailer, or train unit 21 as in FIG. 2d. Pig 20 and trailer unit 21 may be connected together by a coupling 23 that permits articulation, and hence the ability of the train to pass through bends. Trailer unit 21 may include one or more of a power supply, power storage elements such as rechargeable batteries, and data recording equipment. One or the other of pig 20 or trailer unit 21 may include one or more location determining members, such as a counter wheel 25.

Pig 20 has, mounted within shell 22, a magnetic field generator 30 that includes an assembly of magnetic circuit elements 31, and sensing elements 32. Either pig 20 or trailer 21 may have signal processing and data recording elements 34, and at least one power supply element 36, and it may also have a location signal transmitter 38. Magnetic circuit elements 31 may include elements of two primary magnetic circuits 40, 42 that each include a magnet 44, 46 (which may be a cluster of stacked magnets), a first pole member or pole piece 48, 50 and a second pole member or pole piece 52, 54. In one embodiment, the pole pieces are circular discs that extend in planes perpendicular to the long axis (i.e., the axial direction) of pig 20. The pole pieces are magnetizable materials of high magnetic permeability. Magnet 44, first pole piece 48, and second pole piece 52 are all joined in a continuous linking of highly magnetically permeable members. Similarly, magnet 46, first pole piece 50, and second pole piece 54 are all joined in a continuous linking of highly magnetically permeable members. For ease of description, the first pole pieces 48, 50 will arbitrarily be identified as "North", or N, poles, and the second pole pieces will be designated as "South" or S. It could as easily be the opposite. It may be noted that a retainer, which may be in the nature of a non magnetically participating core piece in the nature of a threaded rod 56 is passed co-axially between these two assemblies, and magnetically isolated from them. Inasmuch as the magnets are quite powerful, and their North poles are advanced closely together, there may be a significant tensile force in threaded rod 56. Additional magnetically and electrically isolated threaded fasteners may also be used as indicated at 53 sandwiching the first or N poles 48, 50, 68 and 70 of the primary and secondary magnetic circuits, and at 55, clamping the second, or S poles of the primary and secondary magnetic circuits. A non-magnetically participating gap maintaining member, or spacer 58 may be mounted between first pole pieces 48, 50. Spacer 58 may have the form of a radially extending disc, and have a slim through-thickness. In one embodiment, this distance may be from a few thousandths of an inch to perhaps as much as ¼" depending on the diameter of the magnetic poles and the strength of the fields. It may be desirable for the spacing between the mutually repulsive poles 48 and 50 to be as small as practicable. A spacer may not necessarily be required, given the very strong mutually repulsive forces between the opposed north poles. Magnets 44, 46 may be permanent magnets, and may be rare earth magnets. They may establish a magnetic flux density in their respective pole pieces that is at magnetic saturation.

Magnet circuit elements 30 may also include elements of two secondary magnetic circuits 60, 62 that each include a magnet 64, 66 (which, may be a cluster of stacked magnets), a first pole member or pole piece 68, 70 and a second pole member or pole piece 72, 74. In one embodiment, the pole pieces are annular discs that extend in planes perpendicular to the long axis (i.e., the axial direction) of pig 20. As will be understood, the pole pieces are magnetizable materials of high magnetic permeability. Magnet 64, first pole piece 68, and second pole piece 72 are all joined in a continuous linking of highly magnetically permeable members. Similarly, magnet 66, first pole piece 70, and second pole piece 74 are all joined in a continuous linking of highly magnetically permeable members. For ease of description, the first pole pieces 68, 70 will arbitrarily be identified as "North", or N, poles, and the second pole pieces will be designated as "South" or S., provided that it is the same polarity as the neighbouring pole piece 48, 50, of the primary magnetic circuit.

Magnet 64 (or 66 as may be) may have an annular body that seats concentrically about magnet 44 (or 46 as may be), or it may be made up of a cluster of magnets mounted circumferentially about magnet 44 (or 46) in a common, magnetically permeable path. The magnets and other elements of the outer, secondary magnetic path do not contact the magnet or magnets or other elements of the inner, or primary magnetic path. The repulsive forces involved may be quite substantial. To the extent possible, first pole pieces 68 and 70 of the secondary magnetic circuit are mounted closely adjacent to, but without touching, first pole pieces 48, 50, respectively, of the first magnetic circuit, and second pole pieces 72, 74 are mounted correspondingly tightly adjacent to second pole pieces 52, 54. The second pole pieces need not necessarily be mounted as closely adjacent to, but not touching, each other as the first pole pieces, although it may be convenient to do so. Non-magnetically participating spacers, 76, 77 may be placed between the various neighbouring pole pieces of the primary and secondary circuits to isolate the respective primary and secondary elements and so to prevent the circuits from touching. These spacers may be as thin as a few thousandths of an inch thick, and may not strictly be necessary as the repulsive forces between the members may tend to be quite strong and may tend to maintain a spacing between them of their own accord.

The magnetic flux density at the outer periphery of the pole pieces may tend to be at saturation. The strength of the magnetic field in the secondary circuit may tend to be of a similar order of magnitude to that in the first field, and may, in one embodiment, be of substantially equal strength. The outer diameter of the pole pieces of the secondary circuit may be approximately substantially similar to, or perhaps slightly less than the outer diameter of the pole pieces of the associated primary pole pieces. Inasmuch as the region in which sensing may occur is at or near the radial plane between the two primary circuit North pole pieces, it may be that the apparatus described may be relatively more sensitive to maintaining this relationship as the opposed pole pieces forced closely together (the North poles, as illustrated) than at the more distant, spaced apart poles, (the South poles, as illustrated).

Mounted between the two opposed North pole pieces is a first sensor array 80. Sensor array 80 may include a plurality of sensing members spaced circumferentially about the outside of an array carrier, which is, itself, mounted between the two adjacent primary North poles. To that end, spacer 58, may extend to pole pieces 48, 50, and may be the carrier for sensor array 80. Spacer 58 may be, or may include, a PC board with conductivity vias and layers by which signals from the sensors may be transmitted to and from a suitable data collection bus, and to such recording and data equipment as may be appropriate. Sensor array 80 may include as many as, for example, 250 sensors spaced circumferentially about the radially outermost extremity (i.e., the periphery) of the sensor carrier, e.g., spacer 58. This may tend to give a relatively fine degree of sectoral differentiation between observed readings, and a corresponding level of resolution of magnetic flux variation (or, by proxy, eddy current field divergence) as a function of circumferential location. The pitch spacing of the sectors of sensors 82 is symbolised by $\Theta_{82}$. While it is possible for the pitch spacing to vary, it may be arithmetically convenient for the pitch spacing of the sectors to be equal. In one embodiment each sensor 82 may have the form of Hall effect or GMR sensors (where no change in polarity is expected), with the plane of the face of the sensor lying tangentially, and radially outwardly of, the outer periphery of the pole pieces. Each sensor may be as little as about 2 mm, or somewhat less than 1/8", square. In one embodiment these sensors may be axially offset in two alternating staggered rows. These sensors will tend to be used to measure magnetic flux density in the radial direction. The sensing apparatus may also include a second set or array 86 of sensors 88 each having sensitivity to changes in flux through their face, but little sensitivity to changes in flux through their sides, such as Hall effect sensors, which can sense a change in field polarity. The "sensitive face" may tend to lie in a radially extending plane, such that a normal to the plane of the sensor face may tend to extend in the axial direction. The number of sensors of array 86 spaced about the circumference of the first pole pieces may be quite large, and may be in the hundreds, and may be the same in number as the number of radial axis flux sensors in array 80. Sensors 88 may lie in a plane axially to one side of sensing array 80. The sensing apparatus may further include a third set or array 92 of sensors 94, in which the number of sensors may tend to be the same as that of array 86, and which may tend to include Hall effect sensors similar to sensors 88, which lie in radial planes and have normal vectors in the axial direction. Array 92 may be axially offset from array 86 to the other side of the plane of array 80. The various sensors are connected to signal processing apparatus 34 that samples and measures current in the various sensors, and then processes those values to yield interpretive results from the sampling and measuring process. Alternatively, or additionally, the data may be recorded for subsequent post processing. If field generator 30 and sensor array 80 may be mounted within shell 22 in a manner that interposes shell 22 between sensor array 80 (and field generator 30) and thus both protects the sensors and imposes a standoff between the sensors and the pipewall. Shell 22 may have brackets or other fittings, indicated generically as 90 such as may tend to maintain a spacing, or center, field generator 30 and sensor array 80 within shell 22. In one embodiment, pig 20 may have sprung rollers, or runners 95, such as may tend to encourage pig 20 to be maintained in a generally centered position within pipeline A10.

As may be noted, pig 20, when standing alone, will tend to "leak" magnetic flux from the North poles to the South poles. The arrangement of magnets is such that, at rest, there may tend to be a very high radial flux density in, and immediately adjacent to the central plane 100 between pole pieces 48, 50, which may be the mid-plane of spacer 58. The secondary magnetic field may tend to provide a magnetic impedance between the North and South poles so that the primary magnetic field may tend to be urged or forced to divert to take a longer path, such as may tend to cause the primary field to flow preferentially into the adjacent pipe wall rather more than might otherwise be the case.

When pig 20 is introduced into a pipeline, and assuming the pipe wall to be of a ferromagnetic material such as a mild steel, the magnetic flux that leaks will not be leaking into an infinite air gap, but rather into a relatively small air gap '$G_2$', then into a highly magnetically permeable cylindrical wall, then back across another relatively small air gap back into the far end poles, thus completing the magnetic circuit. The magnetic flux leaking from the central plane is intended to be sufficient to saturate the surrounding cylindrical pipe wall.

Where the pressure differential across pig 20 is substantially constant, and the pumping system can maintain that constant pressure differential, pig 20 may tend to move at approximately constant speed down the pipe. Even if the speed is not precisely constant, the distance counter wheel, and the recording anomalies each time a flanged pipe coupling is passed will provide a record of the progress, and hence the location of pig 20. Inasmuch as the pipe is electrically conductive, and inasmuch as the motion of a magnetic field relative to a conductive loop will tend to cause a current in that loop, motion of the pig along the pipeline will tend to generate electrical currents in the adjacent pipe wall, those currents tending to run perpendicular to the direction of motion of the magnetic field. The electrical loop currents in the pipe wall may tend, in turn, to generate an associated magnetic field, or back EMF, tending to oppose the motion of the pig along the pipe. To the extent that the magnetic fields of the (permanent) magnets of the pig and the back-EMF field generated in the pipe wall are additive, the overall magnetic flux will appear to be tilted, or slanted in the radial and rearwardly axial direction. Sensors 88, 82 and 94 are of a type appropriate for sensing static magnetic fields. These will typically be Hall sensors or possibly GMR sensors where no change in polarity is expected. Sensor 82 measures the radial field strength. Sensors 88 and 94 measure the field divergence. In a stopped condition 88 and 94 will read approximately the same field strength. Assuming that the pipe wall is perfectly round, and the pig is perfectly centered, and the pipe has no defects, the flux sensed at each of sensors 82 will be equal, and the flux sensed in each of sensors 88 will be equal, and the flux sensed in each of sensors 94 will be equal. However, when pig 20 moves along the pie, the flux sensed in each sensor 88 will tend to be greater than the flux sensed in its associated sensor 94, because the magnetic flux field will be axially "tilted" due to the back EMF. The degree of that tilt will depend on the speed at which pig 20 moves along the pipeline. As the tool starts to move the field will drag away from the direction of travel. In the case of FIG. 2a if the tool, (i.e., the sensing apparatus, pig 20), moves left the field from the pole pieces will drag right. This will cause 94 to read a higher field strength than 92, and in an opposite direction. In this way the degree of field drag can be measured.

Figure 3B:
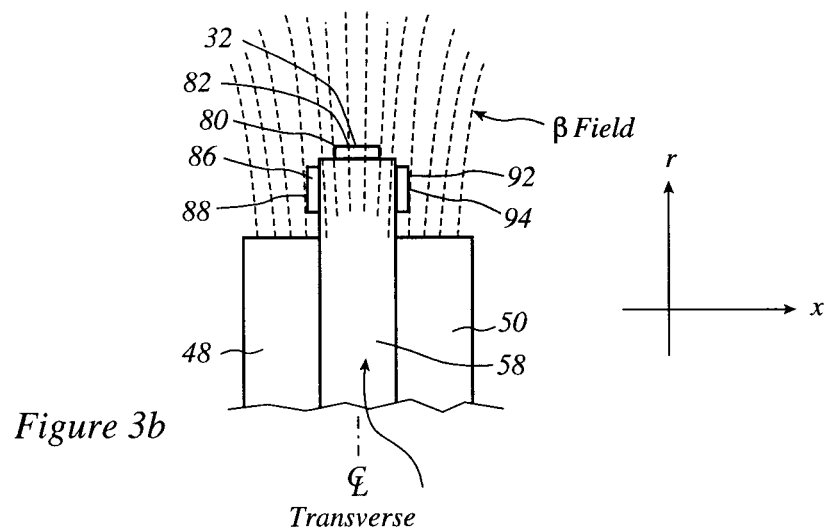
FIG. 3b shows a detail of a sensor arrangement for the pig of FIG. 3a taken on section '3b-3b'.
Figure 3C:
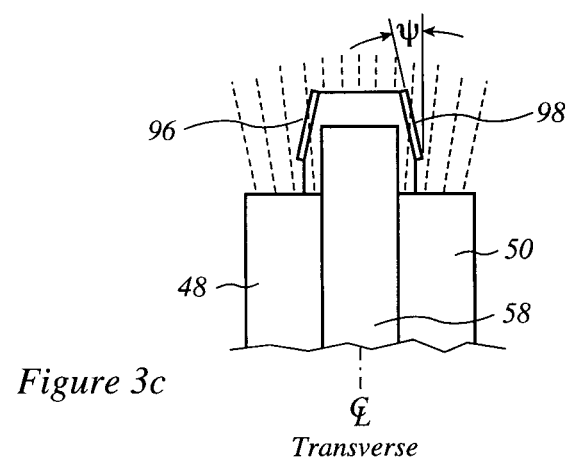
FIG. 3c shows an alternate sensor arrangement to that of FIG. 3b.
Figure 3A:
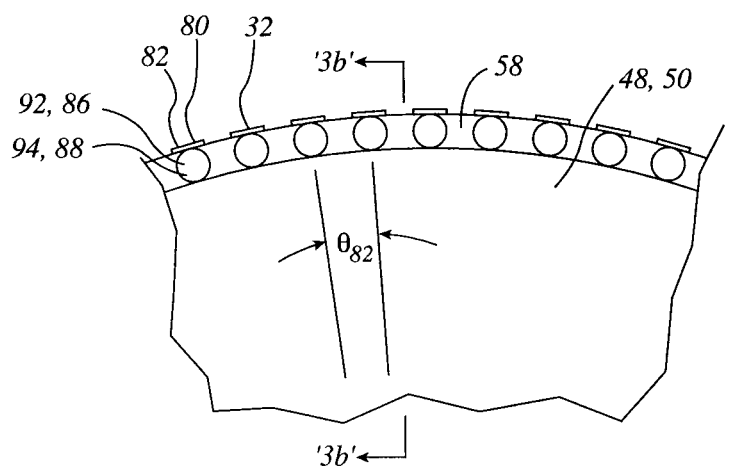
FIG. 3a shows a detail of a sector of the pipeline pig of FIG. 2a looking in the axial direction.

Other arrangements of magnetic field sensors could be employed. For example, in the embodiment of FIG. 3c, two arrays of sensors are indicated as 96 and 98. These sensors are distributed circumferentially about the periphery of spacer 58, much as above. However, they are inclined in the axial direction, (i.e., are angled with respect to the radial plane of spacer 58) such that each sensing loop provides a closed path that encircles both a radial flux region, and an axial flux region. Although the loops need not be spaced on equal circumferential pitches, and although the loops could be individually angled, it is convenient that the arrays be on constant pitches and that the angles of sensors 96 be equal and opposite to the angles of sensors 98. That is, sensors 96 are angled at +phi, and sensors 98 are angled at -phi. The angle phi may be 45 degrees. However, to the extent that sensitivity in the axial direction may need to be rather higher than in the radial direction, and the mean axial and radial flux components may be taken in proportion as the inverse tan of the angle of inclination, phi may be a relatively small angle, in some embodiments less than 20 degrees. Alternatively, each sensor may include several turns in its windings, and it may have separate windings for measuring radial and axial flux, or it may have an intermediate tap at less than the total number of turns of the coil for one or the other.

Figure 3D:
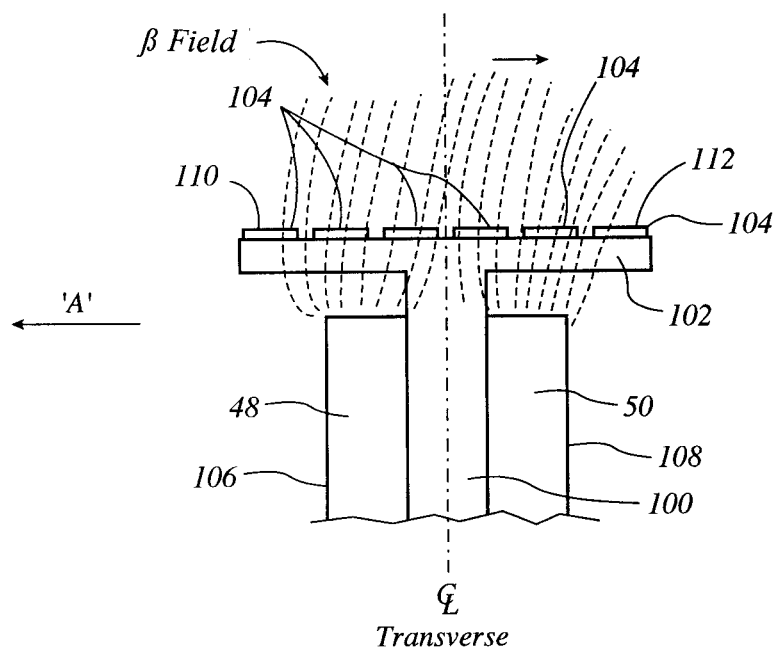
FIG. 3d shows a further alternate sensor arrangement to that of FIG. 3b.
Figure 3E:
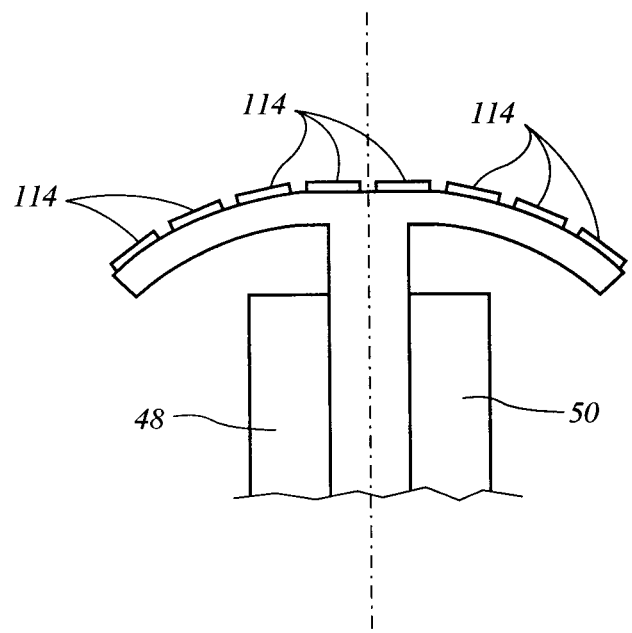
FIG. 3e shows a further alternate sensor arrangement to that of FIG. 3b.

In the alternate embodiment of FIG. 3d, spacer 58 may be supplanted by a spacer, sensor carrier or sensor mounting member (or members) 100, sandwiched between opposed primary pole pieces 48, 50 of the magnetic flux field generator. Member 100 may have a peripheral flange, or widened radially outermost portion (or portions) 102 such as may support a plurality of axially distributed flux sensors 104. There may be as few as two such flux sensors, one mounted to one side of the transverse centerline, and one mounted to the other side. Alternatively, there may be three such sensors, being a central sensor with left and right hand (or upstream and downstream) neighbours. The size and spacing of the sensors may be such as to extend axially beyond the respective upstream and downstream faces 106, 108 of poles 48, 50, such as to stand axially proud thereof, or to straddle the pole, and may stand radially outward (or radially proud) of the peripheral extremities of poles 48 and 50, by some radial stand off distance. In this manner, when the B field drags, there may be a differential flux observed across sensors 104. E.g., the most axially upstream and downstream sensors 110 and sensor 112 may give different readings according to the extent to which the field is tilted or skewed in the direction of drag. Of course, a pig may have both axially spaced sensors lying on a circumferential face, or orientation, as items 104 of FIG. 3d, and sensors lying in a radial plane, such as sensors 88 and 94 of FIG. 3b, angled as in items 96 and 98 of FIG. 3c, or may approximate an arc, as in items 114 of FIG. 3e.

In this system, it may be understood that the largest magnetic resistance is in the generally annular air gaps between the pole pieces and the pipe wall. Since the pipe wall is at saturation, and the pipe wall is several orders of magnitude more magnetically permeable than the air gap, first, the amount of magnetic flux returning across the far end air gaps must be equal to the flux moving across the air gap at the central plane, and, second, a defect in the pipe wall at the far end gaps will tend not to cause a significant (or possibly sensible) variation in the values measured at the sensing arrays at the mid plane. The sensors may tend to be much more highly sensitive to variations in the field very locally in the region of the central plane of the opposed North poles.

To the extent that the overall magnetic flux is constant when the entire circumferential sum is taken, the flux sensed at each of sensors 82 will be a measure of the resistance of the air gap at that point. Thus, even if pig 20 is not centered, the size of the local air gap can be determined (and, indeed, plotted). Since the roundness (or other shape) of the pole pieces is (a) known; and (b) tightly controlled, this calculation may tend to reveal the extent to which the pig is running eccentrically, and whether the pipe is round. Lack of ovality may be determined, and where the lack of ovality is local, the presence of a dent or bulge may be identified.

The flux in sensors 86 and 90 may tend to be sensitive to the extent that the magnetic flux "leans over", i.e., is angled axially out of the radial plane. If there are local variations in the "tilt" as a function of angular position in the circumferential direction, this is an indication of the existence of a local non-homogeneity, or defect. Where there is an axially extending crack in the pipe wall, the electrical circumferential eddy current in the pipe wall will have to work around the crack, lessening the back EMF. Where there is a circumferentially extending crack, or corrosion patch, and the pipe wall is at magnetic saturation, a portion of the magnetic flux may tend to have to flow elsewhere, leading to a reduction in the flux flowing to that portion of the pipe wall, and the "tilt" of the sensed EMF field may momentarily waver, or stick, and then appear to jump the gap or crack. Where there is corrosion and scale, and pitting, the magnetic flux will jump intermittently as it finds and then loses high permeability paths, leading to a rapidly fluctuating signal strength in the various sensor elements.

Although pig 20 and the various pole pieces have been described as being round when viewed in the axial direction, this need not be so. It may be that they could be square, or rectangular, or hexagonal, or star shaped, or some other arbitrary shape, subject to having the signal processing ability to back out from the sensed results both the shape of the pipe wall and anomalies that may be observed. In general, where measurements are to be taken from a substantially round cylindrical object, a substantially round apparatus with a relatively small average gap size may tend to be relatively convenient to construct, and relatively easy to analyse in terms of mathematical manipulation of the resultant data to yield insights into the condition of the pipe wall. That is, the extraction of information from raw data may be on the basis of variation from a datum value. The datum value need not be zero, and the datum value at one sensor need not be the same as the datum value at another sensor. The sum of values in the flux in the radial direction may give an overall measurement of the resistance of the magnetic path. The sectoral (i.e., circumferential or peripheral) spacing of the sensors permits sectoral variation in the field to be measured, both with respect to sectoral datum values and with respect to the values, and variation, of adjacent sectors recorded at the individual sensors. Pig 20 may be ballasted to provide a means for maintaining itself in a generally known, (e.g., upright) orientation.

In the alternate embodiment of FIG. 2b there may be a pig 120 that is substantially the same as pig 20 in construction and principles of operation, but differs therefrom in being formed as an annulus such as to permit flow of a production fluid through a central passage 122 formed within pig shell 124. There is sufficient, flow resistance that pig 120 may still be urged along pipeline A20 by the production flow. Pig 120 may have a flow resistance governor in the nature of a movable vane or valve, indicated as 126, such as may permit longitudinal speed of the pig to be varied, e.g., as when placed in a gas flow line.

In the further alternate embodiment of FIG. 2c, pig 130 is substantially the same as pig 20, but rather than having two opposed primary poles in the nature of 48, 50, pig 130 has a single central primary magnetic circuit pole 132 (which for convenience is designated 'N'). Pole 132 is sandwiched between the poles 68, 70 of like-polarity of the pair of adjacent secondary magnetic circuits 60, 62 all of poles 132, 68, and 70 being mutually repulsive. Again, the secondary magnetic circuits may tend to urge the radially outwardly oriented field of pole 132 to be more tightly or narrowly focused.

The embodiment of FIG. 2d is provided to indicate that the detection apparatus need not be limited to a single observing section. In FIG. 2d a pig 134 may be taken as being the same as pig 20, but instead of having a single magnetic field generator and sensing section, includes two field generator and sensing sections, as at 136 and 138 (their polarities being opposite), should additional readings or greater resolution be desired. In general, such a pig may have two, three, four or more such sections, as may be.

Figure 4:
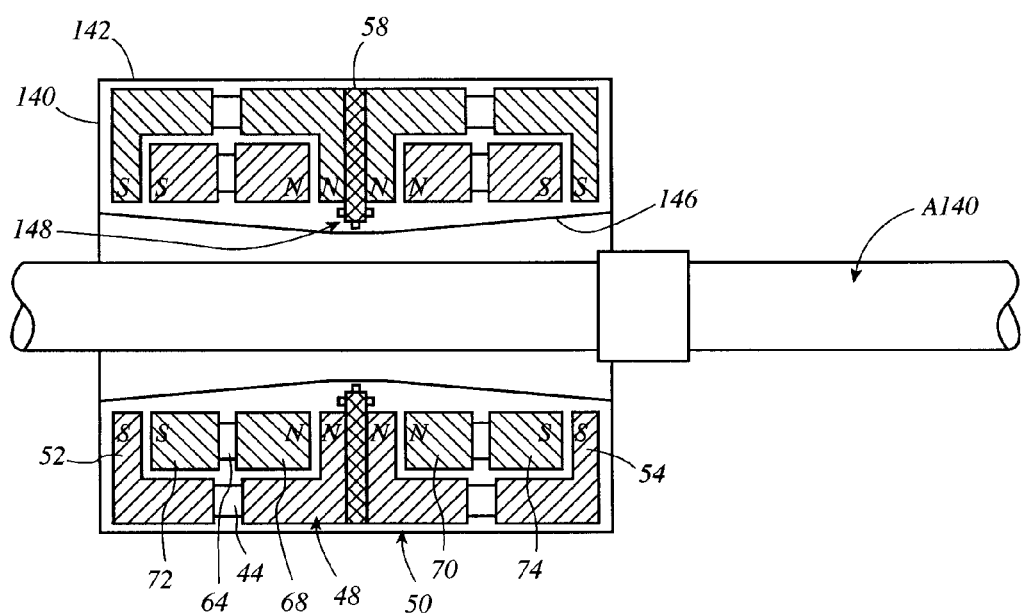
FIG. 4 shows a cross-section of an alternate form of defect detection apparatus to that of FIG. 1b.
Figure 2E:
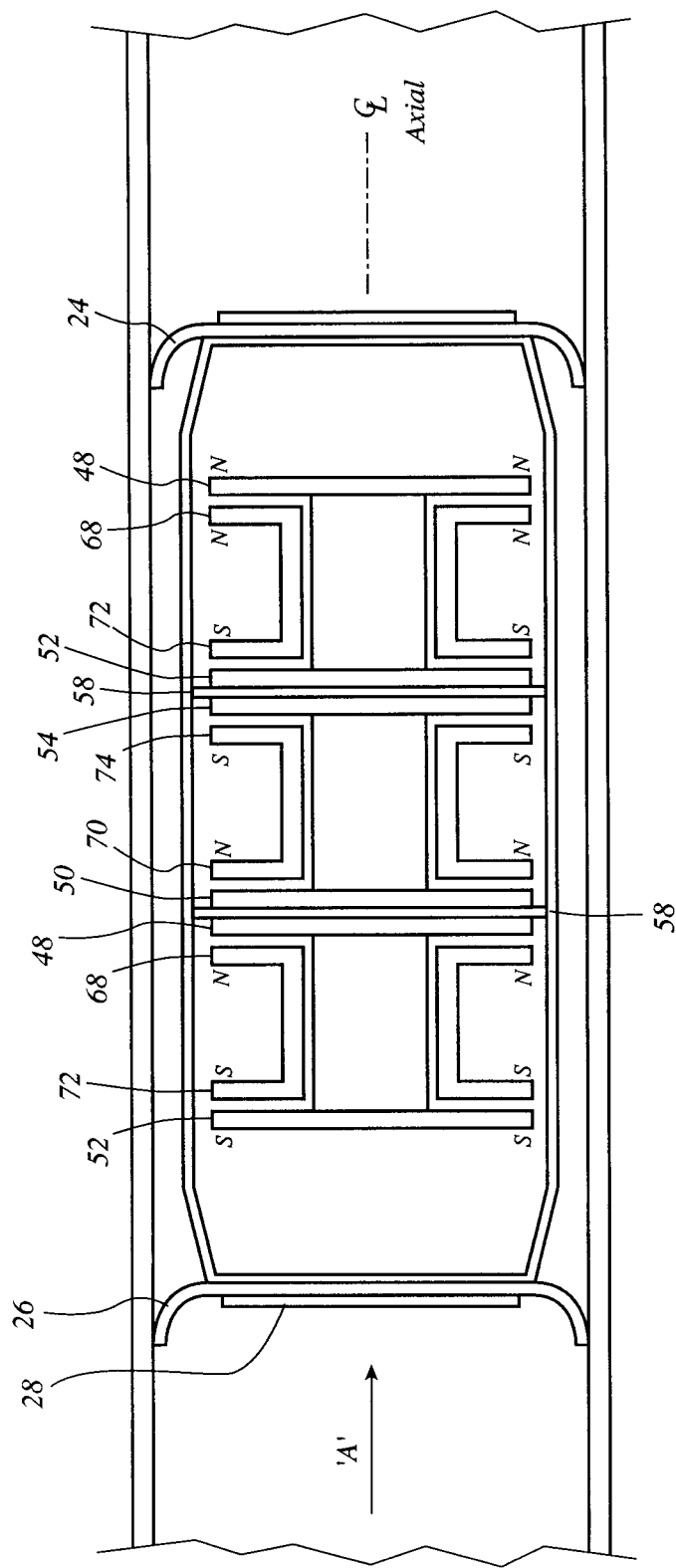
FIG. 2e shows an alternate embodiment of pipeline pig to that of FIG. 2a having more than one magnetic field generator section and more than one sensing section.

The embodiment of FIG. 4, shows an anomaly detection apparatus 140 that is, in essence, pig 20 turned inside-out. That is, rather than having the body to be surveyed surrounding the observation apparatus, (as in the manner that pipe A10 surrounds pig 20 during operation), apparatus 140 has an annular body 142 that surrounds the object to be observed, A140 which may be pipe of a drill string body 142 has an enclosing shell 144 in which there is a field generator 146, and a sensing array 148. Motive power is provided by the drill rig raising and lowering the drill pipe. A computational complication is added if the drill pipe is spinning (i.e., rotating about its longitudinal axis) as it is being drawn past apparatus 140. Apparatus 140 may be used where the internal configuration may tend to be impractical. Applications such as oil well drill pipe or oil well coiled tubing inspection are two possibilities. In this case, as contrasted to pig 20, the magnetic field is focused radially inward instead of outward. While this system is primarily designed for use in pipes, it is possible to use the external system (e.g., of FIG. 4) for solid rods but the ability to detect defects in the center of a thick rod may tend to be limited.

Figure 5:
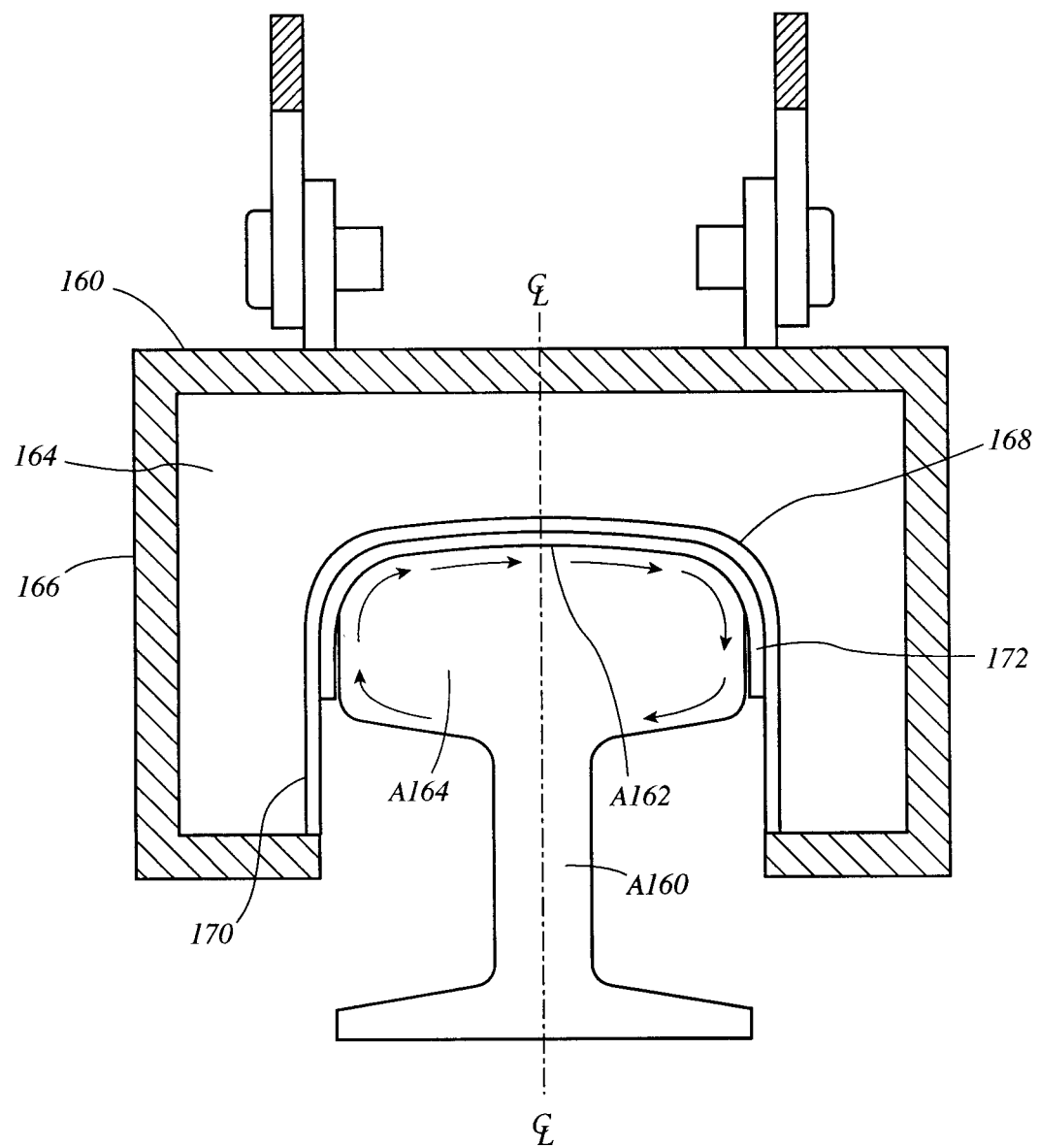
FIG. 5 shows a cross-section of a further alternate form of defect detection device to that of FIG. 1b.

In the further alternate embodiment of FIG. 5, there is an anomaly detector 160 that neither fully surrounds, nor is fully surrounded by, the object to be examined, A160. Detector 160 is substantially similar to pig 20, but differs in effect, by having an open-sided inspection profile. In this instance, object A160 may be a rail of a rail road track. It may be that the majority of defects of interest may lie relatively close to the surface in the upper region A162 of the head A164 of the rail, where pitting, cracking, spalling, and internal defects may most commonly occur. In this instance the North and South pole pieces may be plates, such as North pole plate 164 contained within housing 166. The inner face of plate 164 may have a profile conforming generally to the shape of an unworn rail, as at 168, and the inside face of the profile (and hence the sensing array), may be protected by a non-electromagnetically participating shell 170 that may include, or have mounted to it, a sliding wear member 172 (also electromagnetically non-participating). In this case the axial motive power is provided by a vehicle that is driven along the rails, and that tows or otherwise propels sensing apparatus 160 forward. The towing device may lift apparatus 160 when it encounters switches or diamonds. An array of sensors 174 is mounted about the portion of the profiled periphery of interest. The axial spacing of poles of primary and secondary magnetic circuits may be relatively small, and may be of similar magnitude to that of the spacing between primary poles 48 and 50.

The pipeline inspection apparatus, i.e., pig 20 or pig 120 may be employed to seek information permitting the measurement, or estimation, of internal and external corrosion, axial and circumferential cracks, and the magnitude of ovality and denting, if any. The embodiments of defect detectors described herein may tend to permit pipe wall examination or sensing, without the field generator or the sensors having to touch, let alone ride against, the pipe wall. That is, shell 22 (or 122) may tend to permit the sensors to be protected, and sealed from the production (or other) fluids.

The field generator (i.e., the magnetic circuit elements) of this inspection apparatus may tend to emit a relatively strong and mostly parallel, disc shaped magnetic field. The plane of the disc is perpendicular to the pipeline axis such that the emitted field is predominantly normal to the surface of the wall of the adjacent object to be inspected. Each of the three defect types, cracks, corrosion and dents, are measured using different effects of the magnetic field generator.

Figure 1B:
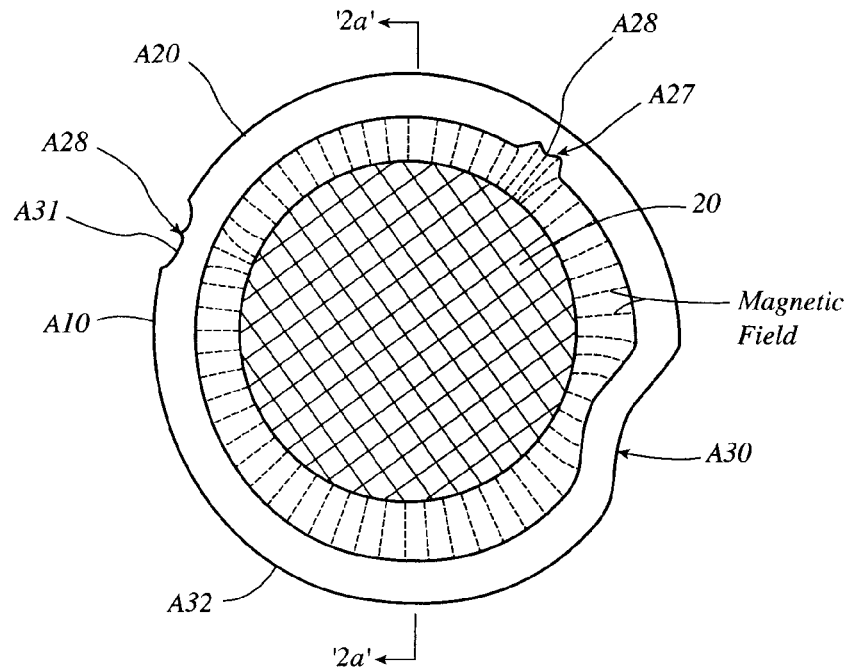
FIG. 1b is a conceptual cross-section of a pipeline pig having a defect detection apparatus, located within a pipeline having a variety of defects.
Figure 1C:
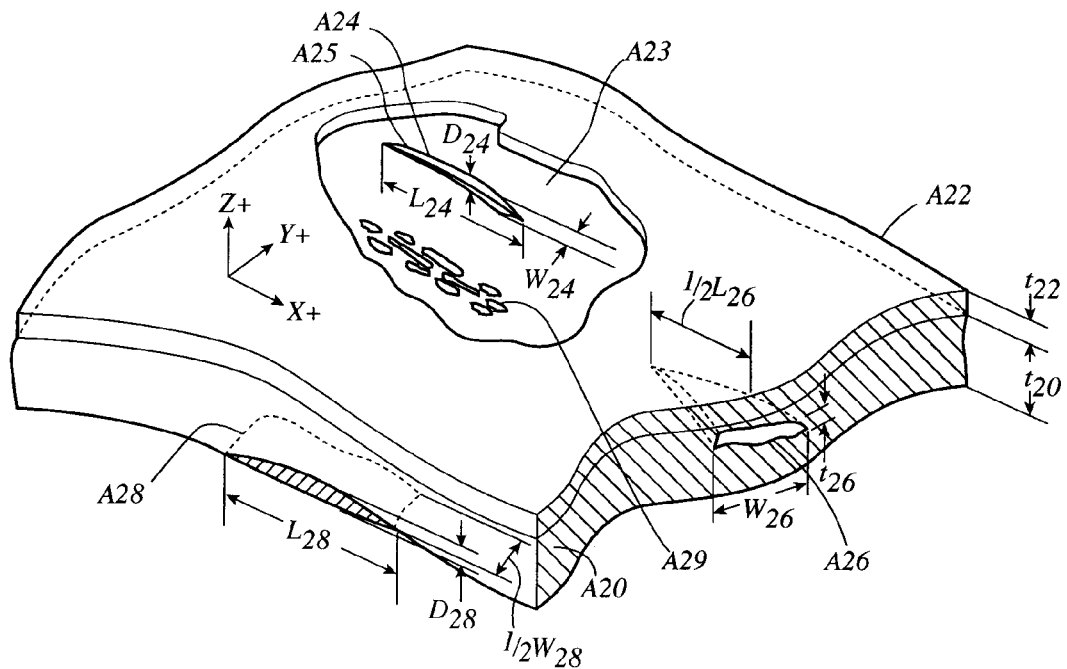
FIG. 1c is a perspective view of a portion of the pipeline of FIG. 1a, illustrating a number of the defects of the pipeline of FIG. 1b.
Figure 1D:
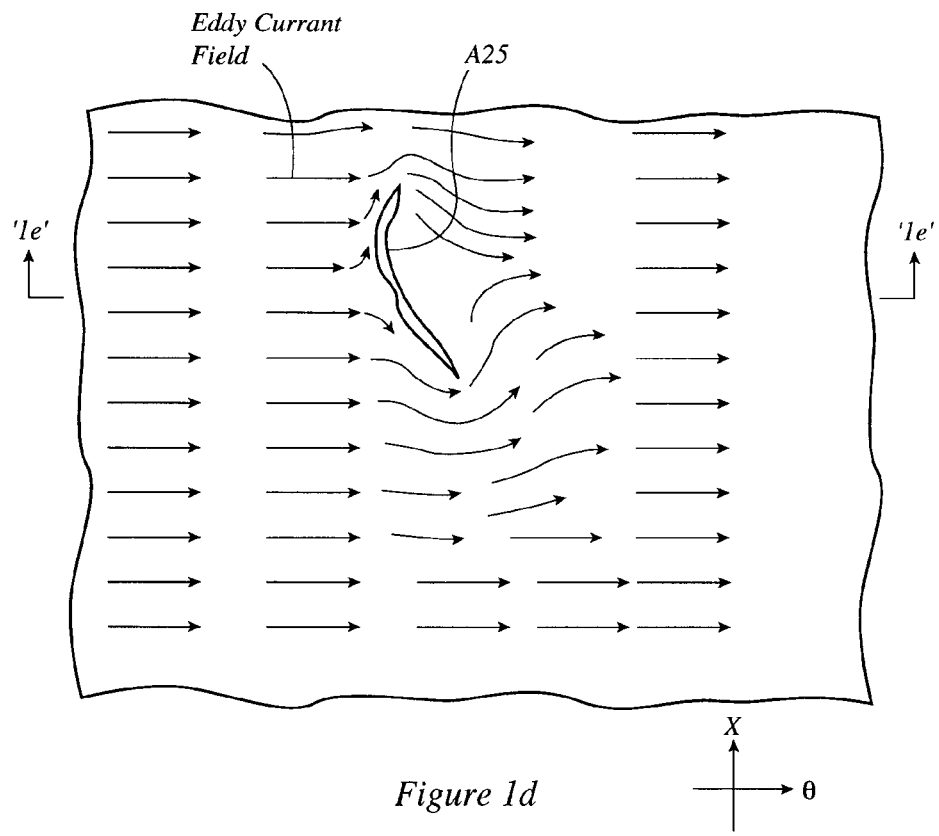
FIG. 1d is a developed view of a portion of a pipeline wall showing, conceptually, divergence of an induced electrical eddy current field in the neighbourhood of an anomaly in the pipe wall.
Figure 1E:
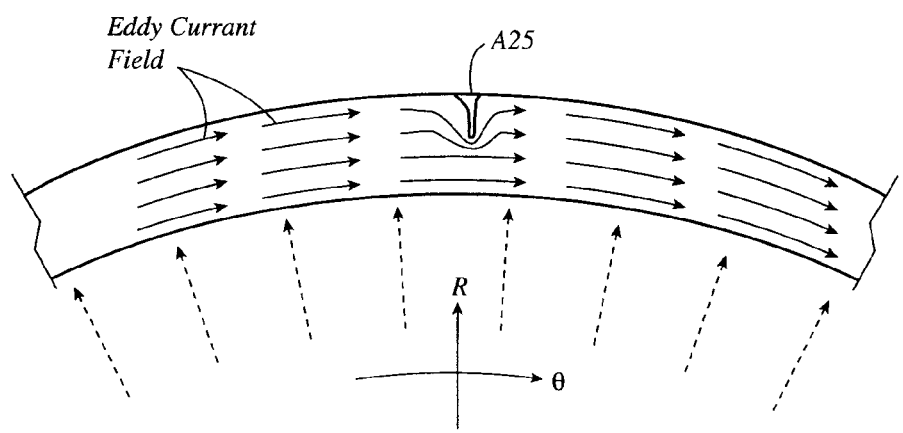
FIG. 1e is a cross-section of a portion of the pipeline wall of FIG. 1d, taken on section '1e-1e' showing the induced eddy current field in the region of the anomaly.

Cracks in the pipe wall are measured using eddy currents. In this case the eddy current is generated in the pipe wall when the field generator is in motion. The generated eddy currents move circumferentially in the pipe wall and are perpendicular to the longitudinal axis of the pipe. The magnitude of the eddy current is determined by the local magnetic field strength and the velocity of the field generator. Note that the velocity is a function of both the axial velocity and the rate of rotation of the field generator. Normally the rate of rotation may tend to be very small, and as such may be ignored. FIGS. 1d and 1e show a schematic or conceptual representation of the eddy current flow in a portion of a plate or shell in the region of an anomaly, A25. Well away from anomaly A25, the eddy current field is substantially uniform or regular, and the associated back-EMF field associated with those eddy currents is regular and relatively even or uniform. When the eddy current field encounters a crack, such as anomaly A25 with a longitudinal component, the eddy current field is forced to deviate around the crack. As illustrated in the figures, the eddy current deviates both around and below the crack defect. This has the effect of generating a localized change in the eddy current density, and hence a local change in the back-EMF associated with the eddy current field that is abnormal as compared to the field that would be observed generally elsewhere. As the field generator moves along the pipe, it omits a moving wave-front, pulse, of magnetic flux. The magnetic flux passed into the pipewall as the wave passes causes eddy currents in the wall. The magnitude of the eddy currents, and their direction is proportional to the time rate of change of the imposed magnetic field. These eddy currents in turn generate a magnetic field that opposes the field generator's magnetic field, i.e., a back EMF. To the extent that the leading edge of the eddy current may tend to yield a back EMF that is opposite in direction to the trailing edge eddy current, the sensed magnetic field may appear to be tilted. The net result is that the magnetic field from the field generator appears to "drag", i.e., appears to lag behind at an angle. The degree of drag is dependent on the local eddy field strength. As the local eddy current density increases or decreases the field drag increases or decreases. By measuring the degree of field drag, and combining that information with corrosion data, the degree of cracking can be determined.

Ovality and corrosion may tend to be determined by measuring the local radial strength of the magnetic field emitted by the field generator. FIG. 1b shows a cross sectional view of the magnetic field distortions that may occur for the various defects. Inward dents may cause a local increase in field density (since there is an apparent local reduction in resistance of the air gap), with a local decrease in field density at the edges. Corrosion may tend to manifest with the opposite effect. Internal corrosion may typically show a steeper field gradient than external corrosion. It may be noted that as the axial velocity of the field generator increases the ability to detect external cracks and corrosion may tend to degrade. In general the velocities have to be fairly high for this to happen, and may occur at velocities that may be greater than 10 m/s (36 km/h).

The field generator 30 of pig 20, for example, has a pair of closely spaced magnets whose poles oppose each other, as in the manner of pole pieces 48, 50. In this case the North poles are facing each other. This may tend to produce a locally strong magnetic field that is concentrated radially around the longitudinal axis (i.e., is concentrated in a radial disc extending away from the longitudinal axis). In a pipeline pig application the gas (e.g., air, natural gas etc.), liquid or quasi-liquid fluid (e.g. oil, water, or slurry) in the gap between (a) the outer circumferential edges of the primary field generator pole pieces and (b) the pipe wall, acts as a resistance to the magnetic field. As the size of the gas or fluid gap increases, a higher percentage of the magnetic flux of the primary field may tend to travel directly from pole-to-pole in the gas or liquid gap. The secondary field generator creates a blocking field that may tend to force or urge the magnetic flux or the primary field to move into the pipe wall. The effect is to tend to make the magnetic lines of force at the center of the field generator move parallel in the radial direction into the pipe wall. It may also tend to enhance the ability of the magnetic field to be affected by defects on the far side of the pipe. The physical dimensions of the field generator are dependent on the pipe diameter, bend radius, and restriction clearance requirements. The spacing (i.e., isolation or segregation) of the primary field generator from the secondary field generator is described above.

Inasmuch as the field generator and sensor assembly is contained within shell 22 (or 122 or as may be), unlike existing intelligent pigs, they do not need to be in contact with the pipewall for sampling to occur, and so may tend not to be affected by debris; weld heads, or other deposits in the pipeline.

There is no specific requirement that the field generator be round, oval and rectangular shapes are also possible. However, these configurations of irregular geometry may tend to require special post processing compensations to correct for the basic irregular field strengths that are generated.

Various embodiments have been described in detail. Since changes in and or additions to the above-described examples may be made without departing from the nature, spirit or scope of the invention, the invention is not to be limited to those details.

I claim:

1. An intelligent pipeline pig for insertion in a pipeline having a cylindrical pipe wall, said intelligent pipeline pig having:
    a body and flux sensors mounted within said body, said sensors being operable from within said body to monitor properties of said pipeline while said intelligent pipeline pig is within said pipeline and said sensors are enclosed within said body;
    a magnetic flux field generator operable to pass magnetic flux across a gap into the pipeline pipe wall; and
    said sensors being mounted to monitor flux drag in said gap.

2. The intelligent pig of claim 1 wherein said magnetic field generator includes a pole piece having a periphery oriented to face the pipe wall, said gap being defined between said periphery of said pole piece and the pipewall; said magnetic field flux sensors are mounted peripherally about said magnetic field generator, and said magnetic flux field sensors are operable to sense sectoral magnetic flux variation adjacent to said periphery of said pole piece.

3. The intelligent pipeline pig of claim 1 wherein said pig includes a standoff to prevent said sensors from touching the pipe wall.

4. The intelligent pipeline pig of claim 1 wherein said body comprises a closure member by which said sensors may be sealed within said body; said sensors are at least one of (a) electrical sensors; (b) magnetic sensors; and said body includes a shell that is substantially electro-magnetically transparent.

5. The pig of claim 1 wherein said sensors include eddy current divergence sensors.

6. The pipeline pig of claim 1, the cylindrical pipeline having a centerline and defining a lengthwise direction along the centerline, and a radial direction away therefrom, and wherein:
    said magnetic flux generator includes a first primary magnetic circuit and a second primary magnetic circuit, a first secondary magnetic circuit and a second secondary magnetic circuit;
    said first primary magnetic circuit and said second primary magnetic circuit are spaced from each other in the lengthwise direction;
    said first primary magnetic circuit includes a first pole piece and a second pole piece spaced lengthwise therefrom;
    said second primary magnetic circuit has a first pole piece and a second pole piece spaced lengthwise therefrom;
    said first secondary magnetic circuit includes a first pole piece and a second pole piece spaced lengthwise therefrom;
    said second secondary magnetic circuit has a first pole piece and a second pole piece spaced lengthwise therefrom;
    said first pole pieces are all mutually repulsive, and are located side-by-side in non-touching proximity next to each other with said first pole pieces of said first and second primary magnetic circuits being beside each other and bracketed between said first pole pieces of said secondary magnetic circuits; and said magnetic flux sensors are mounted peripherally about said magnetic field generator, and are operable to sense sectoral magnetic flux variation adjacent to and peripherally about said first pole pieces of said primary magnetic circuits as a function of circumferential position.

7. A pipeline pig for insertion in a pipeline, the pipeline having an electrically conductive pipe wall, said pipeline pig having a longitudinal axis defining an axial direction, and a periphery radially distant from said longitudinal axis, wherein:

said pig includes a magnetic field generator for passing magnetic flux into said pipe wall;

said pig has an array of magnetic flux sensors mounted about said magnetic field generator, said flux sensors being operable to permit independent monitoring of magnetic flux where the magnetic flux is passed into said pipe wall at a plurality of sectors about said magnetic field generator;

said magnetic flux generator includes a first magnetic circuit and a second magnetic circuit, said first and second magnetic circuits being segregated from each other, and lengthwise adjacent to each other in the axial direction, and one of (a) each of said first and second magnetic circuits having a respective first pole oriented cross-wise to said axis, said first poles of said first and second magnetic circuits being placed next adjacent to each other; said first poles of said first and second magnetic circuits being mutually repulsive; and said sensors being operable to sense axial variation in magnetic flux relative to said first poles of said first and second magnetic circuits; and (b) said flux sensors include at least a first set of sensors and a second set of sensors, said first set of sensors being mounted about said magnetic field generator in a first orientation relative to said magnetic field generator, and said second set of sensors being mounted about said magnetic field generator in a second orientation relative thereto, and combined readings of sensors in said first and second sets of sensors permitting radial and axial components of magnetic flux to be sensed in at least two of said plurality of sectors.

8. The pipeline pig of claim 7 wherein said pipeline pig satisfies part (a) of claim 7, and wherein:

said first and second magnetic circuits are first and second primary magnetic circuits;

said pig includes first and second secondary magnetic circuits, each of said secondary magnetic circuits having a respective first pole;

said first poles of said first and second primary magnetic circuits and said first poles of said secondary magnetic circuits all being mutually repulsive;

said first poles of said first and second primary magnetic circuits being placed in side-by-side non-touching proximity to each other and to said respective first poles of said first and second secondary magnetic circuits; and said first poles of said first and second primary magnetic circuits are bracketed by said first poles of said first and second secondary circuits.

9. The pipeline pig of claim 7 wherein:

said magnetic flux generator includes a first magnetic circuit and a second magnetic circuit, said first and second magnetic circuits being segregated from eachother;

each of said first and second magnetic circuits has a respective first pole, said first poles of said first and second magnetic circuits being placed next adjacent to each other;

said first poles of said first and second magnetic circuits being mutually repulsive; and said first poles defining a peripherally extending interface of one polarity of said magnetic field generator at which magnetic flux is passed from said generator to said pipe wall.

10. The pipeline pig of part (a) of claim 7 wherein:

said first pole of said first primary magnetic circuit has a pole piece that includes a disc extending radially away from said longitudinal axis;

said magnetic field generator passes magnetic flux from said pole piece of said first pole of said first primary magnetic circuit into the electrically conductive wall across a gap;

motion of said pipeline pig along the pipeline causing a magnetic field wavefront to move along said pipeline, said wavefront being oriented cross-wise relative to the pipeline; and said sensors being mounted peripherally about said at least one pole piece adjacent the gap and being oriented to monitor magnetic flux drag during motion of said pipeline pig along the pipeline.

11. A pipeline pig according to part (a) of claim 7 wherein:

said first poles of said first and second magnetic circuits lie side-by-side in non-touching proximity to each other;

said sensors include a first set of sensors and a second set of sensors;

said first set of sensors are oriented to lie predominantly in a radial plane adjacent to said first pole of said first magnetic circuit; and said second set of sensors being oriented to lie predominantly in a circumferential-axial surface adjacent to said first pole of said first magnetic circuit.

12. A pipeline pig according to part (a) of claim 7 wherein:

said pig has a longitudinal centerline;

said sensors include a first set of sensors and a second set of sensors;

said first set of sensors being oriented to lie predominantly in a conical surface relative to said centerline; and said second set of sensors being oriented to lie in other than said conical surface.

13. A pipeline pig according to part (a) of claim 7 wherein:

said pig has a longitudinal centerline, said sensors include a first set of sensors and a second set of sensors;

said first set of sensors being oriented to lie predominantly in a conical surface relative to said centerline;

said second set of sensors being oriented to lie in other than said conical surface;

said conical surface is a first conical surface whose apex intersects said longitudinal centerline to one side of said first pole of said first magnetic circuit; and said second set of sensors lies in a second conical surface whose apex lies to the other side of said first pole of said first magnetic circuit.

14. A pipeline pig according to part (a) of claim 7 wherein one of:

(a) said array of flux sensors includes sensors differentially positioned in both axial and circumferential directions;

(b) said first set of sensors includes sensors lying predominantly in a circumferential-axial orientation;

said second set of sensors includes sensors lying in an orientation that is angularly skewed relative to said circumferential-axial orientation; and (c) said first set of sensors includes sensors lying predominantly in a circumferential-axial orientation;
said second set of sensors includes sensors lying in an orientation that is angularly skewed relative to said circumferential-axial orientation; and
said sensors of said second set of sensors are oriented substantially at right angles to said sensors of said first set of sensors.

15. The pipeline pig of claim 7 wherein said flux sensors are operable to sense magnetic flux as a function of circumferential position.

16. The pipeline pig of claim 7 wherein said array includes sensors mounted to observe eddy field divergence in the pipeline wall.

17. The pipeline pig of claim 7 wherein said pipeline pig has a standoff positioned to prevent said array of sensors from contacting the pipeline wall.

18. The pipeline pig of claim 7 wherein said array of sensors is enclosed within a housing of said pig.

19. The intelligent pipeline pig of claim 1 wherein:
said magnetic field generator includes first and second primary magnetic circuits, said first and second primary magnetic circuits being mutually segregated from each other; and
said first and second primary magnetic circuits each have a first pole, said respective first poles being mutually repulsive, said first poles being positioned closely adjacent to each other.

20. The intelligent pipeline pig of claim 1 wherein:
said magnetic field generator includes at least a first primary magnetic circuit having a first pole and a second pole, and a least a first secondary magnetic circuit having a first pole and a second pole;
said respective first poles being mutually repulsive;
said respective second poles being mutually repulsive;
said first pole of said secondary magnetic circuit being positioned next adjacent to said first pole of said primary magnetic circuit;
said second pole of said secondary magnetic circuit being positioned between said first pole of said secondary magnetic circuit and said second pole of said primary magnetic circuit; and
said secondary magnetic circuit being nested next to said first primary magnetic circuit.

21. The intelligent pipeline pig of claim 1 wherein:
said magnetic field generator includes first and second primary magnetic circuits, said first and second primary magnetic circuits each having a respective first pole;
said first primary magnetic circuit and said second primary magnetic circuit are spaced from each other in the lengthwise direction;
said magnetic field generator includes first and second secondary magnetic circuits;
said secondary magnetic circuits each having a respective first pole;
said first poles of said first and second primary magnetic circuits and said first poles of said first and second secondary magnetic circuits all being mutually repulsive; and
said first poles of said first and second primary magnetic circuits being closely spaced apart, and said first poles of said first and second primary magnetic circuits being bracketed in non-touching proximity by said first poles of said first and second secondary magnetic circuits.

22. The pig of claim 1 wherein said sensors are at least one of (a) electrical sensors; (b) magnetic sensors; and said body includes a shell that is substantially electro-magnetically transparent.

23. The pig of claim 1 wherein said pig has at least one of (a) ends that are narrowed relative to said body more generally; and (b) ends having resilient pipe wall following cups mounted adjacent thereto.

24. The pig of claim 1 wherein said sensors are magnetic field flux sensors mounted peripherally about said magnetic field generator, and said sensors are operable to sense sectoral magnetic flux variation.

25. The pig of claim 1 wherein said sensors include eddy current divergence sensors.

* * * * *